(12) United States Patent
Sata et al.

(10) Patent No.: US 9,144,415 B2
(45) Date of Patent: Sep. 29, 2015

(54) CAROTID-ARTERY-PLAQUE ULTRASOUND-IMAGING METHOD AND EVALUATING DEVICE

(75) Inventors: Masataka Sata, Tokushima (JP); Hirotsugu Yamada, Tokushima (JP)

(73) Assignee: THE UNIVERSITY OF TOKUSHIMA, Tokushima-Shi (JP)

( * ) Notice: Subject to any disclaimer, the term of this patent is extended or adjusted under 35 U.S.C. 154(b) by 261 days.

(21) Appl. No.: 13/637,457

(22) PCT Filed: Jan. 31, 2011

(86) PCT No.: PCT/JP2011/052459
§ 371 (c)(1),
(2), (4) Date: Nov. 6, 2012

(87) PCT Pub. No.: WO2011/118267
PCT Pub. Date: Sep. 29, 2011

(65) Prior Publication Data
US 2013/0044931 A1    Feb. 21, 2013

(30) Foreign Application Priority Data
Mar. 26, 2010  (JP) ................................. 2010-073153

(51) Int. Cl.
*G06K 9/00*    (2006.01)
*A61B 8/08*    (2006.01)
(52) U.S. Cl.
CPC ............. *A61B 8/0891* (2013.01); *A61B 8/5223* (2013.01)
(58) Field of Classification Search
None
See application file for complete search history.

(56) References Cited

U.S. PATENT DOCUMENTS 5,793,883  A  *  8/1998  Kim et al. ...................... 382/128
7,248,725  B2 *  7/2007  Zwirn et al. ................... 382/128
(Continued)

FOREIGN PATENT DOCUMENTS

JP     2007-7387      1/2007
JP     2009-500410    1/2009
(Continued)

OTHER PUBLICATIONS

Kawasaki et al. "Noninvasive Quantitative Tissue Characterization and Two-Dimensional Color-Coded Map of Human Atherosclerotic Lesions Using Ultrasound Integrated Backscatter," Journal of the American College of Cardiology, vol. 38, No. 2, 2001, pp. 486-492.*

(Continued)

*Primary Examiner* — Vu Le
*Assistant Examiner* — Samah Beg
(74) *Attorney, Agent, or Firm* — Mori & Ward, LLP

(57) ABSTRACT

The carotid artery plaque properties are quantitatively determined by a carotid artery echo whereby predicting incidence of cerebral infarction or myocardial infarct. A method includes obtaining, coloring, and displaying steps. In the obtaining step, the integrated amounts per unit time of echo signals corresponding to pixels of an echo image of carotid artery plaque are obtained. The signals are obtained when the image is obtained by an IBS method. In the coloring step, the relationship between ranges and colors is referenced. The available full range of the integrated amount is previously divided into the ranges. The colors are assigned to the ranges. The pixels are classified into the ranges in accordance with the integrated amounts corresponding to the pixels. The pixels of the image are colored in colors corresponding to the ranges of the pixels. In the displaying step, the colored echo image is displayed on a display portion 30.

17 Claims, 13 Drawing Sheets

(56) References Cited

U.S. PATENT DOCUMENTS

| | | | |
|---|---|---|---|
| 2004/0260180 | A1 | 12/2004 | Kanai et al. |
| 2006/0269112 | A1 | 11/2006 | Ochi |
| 2009/0214114 | A1* | 8/2009 | Bengtsson et al. ............ 382/170 |
| 2010/0331698 | A1 | 12/2010 | Tonomura |
| 2011/0098563 | A1 | 4/2011 | Osaka |
| 2012/0070047 | A1* | 3/2012 | Johnson ........................ 382/128 |
| 2012/0243764 | A1* | 9/2012 | Dey et al. ...................... 382/131 |
| 2013/0337501 | A1* | 12/2013 | Takeda et al. ................... 435/39 |
| 2015/0080729 | A1* | 3/2015 | Miyachi ........................ 600/443 |

FOREIGN PATENT DOCUMENTS

| | | |
|---|---|---|
| JP | 2009-530068 | 8/2009 |
| WO | WO 03/015635 | 2/2003 |
| WO | WO 2009/104525 | 8/2009 |
| WO | WO 2009/154133 | 12/2009 |

OTHER PUBLICATIONS

Joakimsen et al. "Reproducibility of ultrasound assessment of carotid plaque occurrence, thickness, and morphology. The Tromsø Study." Stroke, Nov. 1997; vol. 28(11): p. 2201-2207.*

Kawahara et al., "Comparison of Carotid Ultrasonography and High-resolution MRI for Detecting Soft Plaque", Neurosonology 2005, P69-73, 18(2-3).

Okubo et al., "Tissue Characterization of Coronary Plaques", Circulation Journal, Oct. 2008, p. 1631-1639, vol. 72.

Watanabe et al., "Stabilization of Carotid Atheroma Assessed by Quantitative Ultrasound Analysis in Nonhypercholesterolemic Patients With Coronary Artery Disease", Journal of the American College of Cardiology, 2005, vol. 46, No. 11.

Honda et al., "Echolucent Carotid Plaques Predict Future Coronary Events in Patients With Coronary Artery Disease", Journal of the American College of Cardiology, 2004, vol. 43, No. 7.

Naoto Katakami, "Keidomyaku Echo-ho no Rinsho Torikata to Yomikata Choonpa Koho Sanran (IBS)", Modern Physician, vol. 27, No. 10, Kabushiki Kaisha Shinko Igaku Shuppansha, Oct. 15, 2007, pp. 1402-1405.

Hirofumi Shimada, "Integrated Backscatter Kaiseki O Mochiita Keidomyaku Plaque no Teiryoteki Choonpa Kido Kaiseki", Neurosonology, vol. 18, No. 1, The Japan academy of Neurosonology, Jul. 2005, pp. 24-28.

Yeong-Jin Kim, "Ultrasonic Tissue Characterization of Carotid Plaques Using Integrated Backscatter", Surgery for Cerebral Stroke, vol. 29, No. 6, Japanese Society on Surgery for Cerebral Stroke, Nov. 30, 2001, pp. 402-407.

International Search Report for corresponding International Application No. PCT/JP2011/052459, Mar. 22, 2011.

International Preliminary Report on Patentablility (Chapter II) for corresponding International Application No. PCT/JP2011/052459, Mar. 22, 2011, Jan. 19, 2012.

* cited by examiner

ONE MONTH LATER

ONE MONTH LATER

FIG. 3A
FIG. 3B
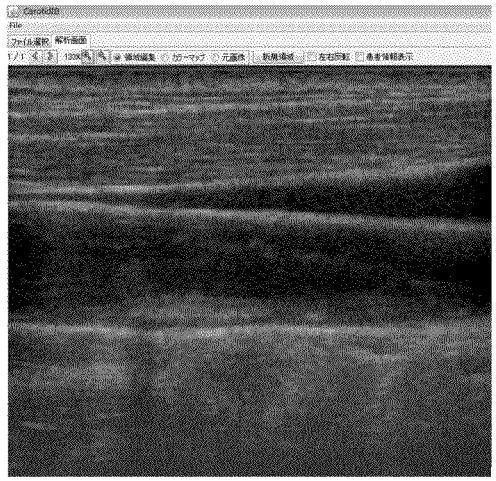
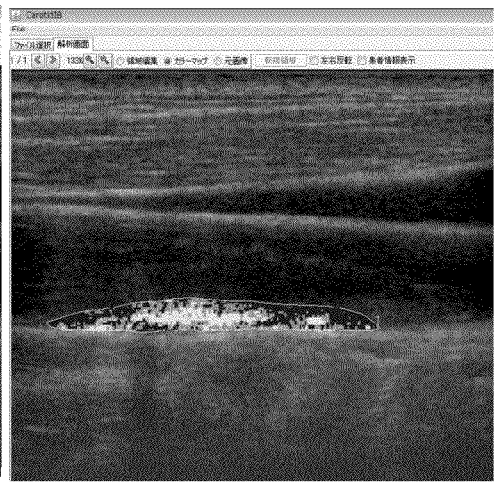
FIG. 4A
FIG. 4B
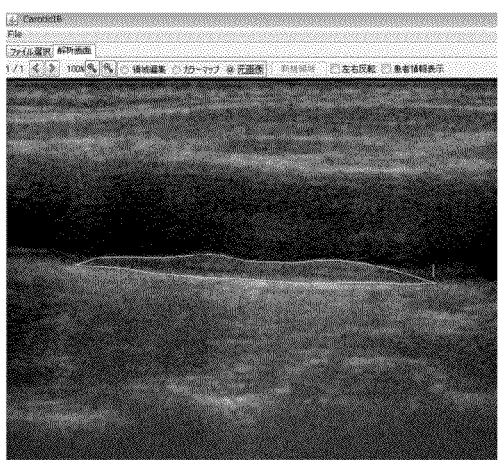
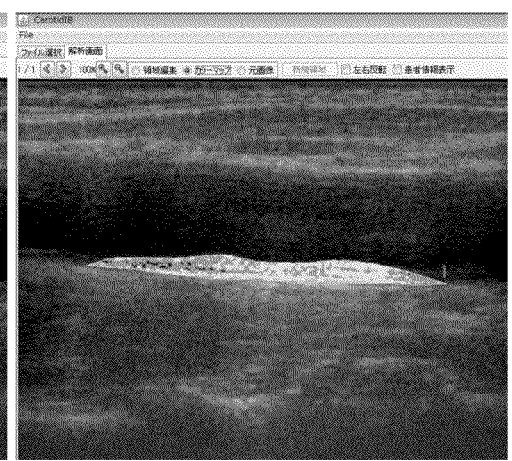

FIG. 5A
FIG. 5B
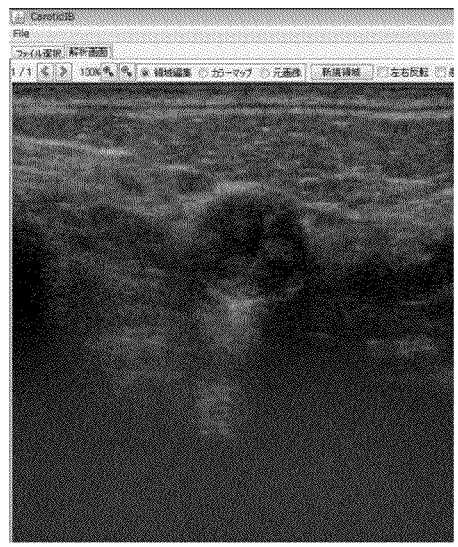
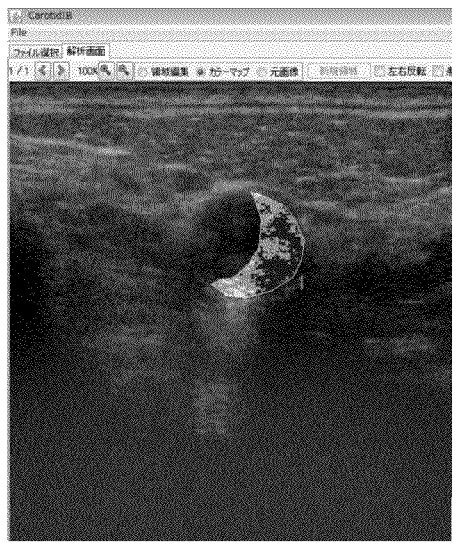
FIG. 6A
FIG. 6B
FIG. 6C
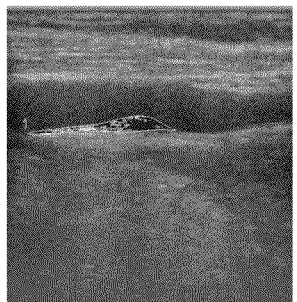
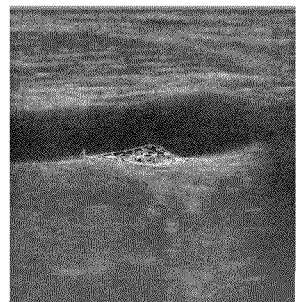
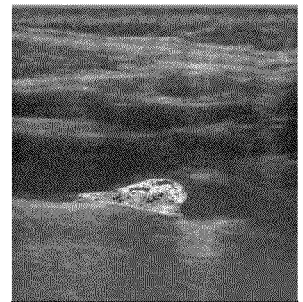
| AREA (cm²) | 20.5 |
|---|---|
| MAX. IB VALUE | −46.9 |
| MIN. IB VALUE | −87.1 |
| MEAN IB VALUE | −70.8 |
| SD VALUE | 0.2 |
| IB MEDIAN | −71.4 |
| AREA (cm²) | 19.9 |
|---|---|
| MAX. IB VALUE | −41.1 |
| MIN. IB VALUE | −87.0 |
| MEAN IB VALUE | −64.7 |
| SD VALUE | 0.2 |
| IB MEDIAN | −65.7 |
| AREA (cm²) | 41.1 |
|---|---|
| MAX. IB VALUE | −31.3 |
| MIN. IB VALUE | −81.2 |
| MEAN IB VALUE | −60.8 |
| SD VALUE | 0.2 |
| IB MEDIAN | −62.0 |

FIG. 9A
FIG. 9B
FIG. 9C
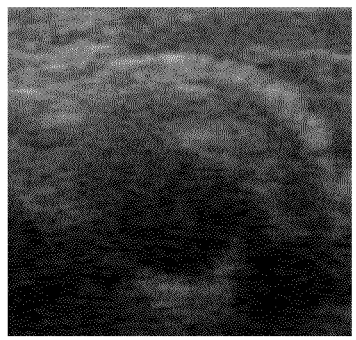
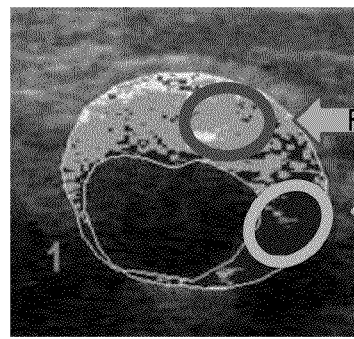
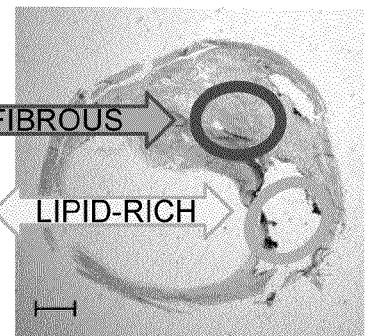
FIG. 10A
FIG. 10B
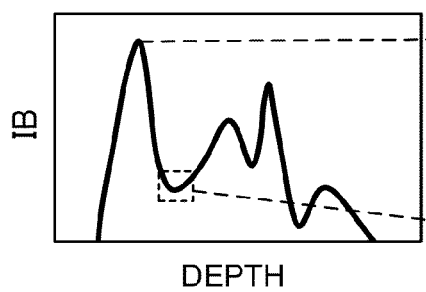
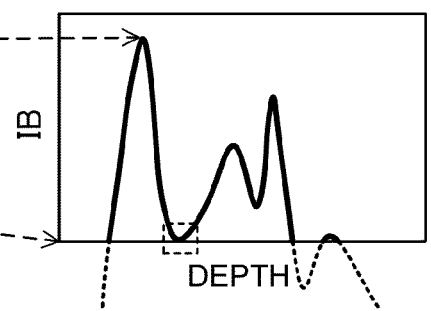
FIG. 10C
FIG. 10D
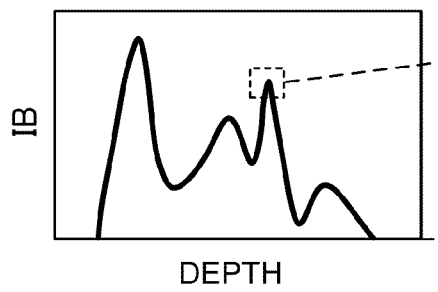
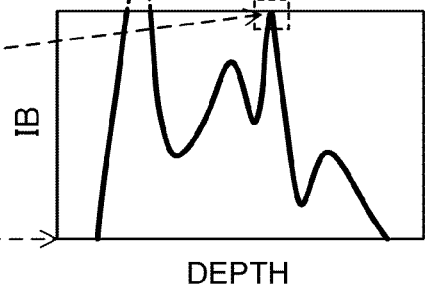

FIG. 17A
FIG. 17B
FIG. 17C
FIG. 18
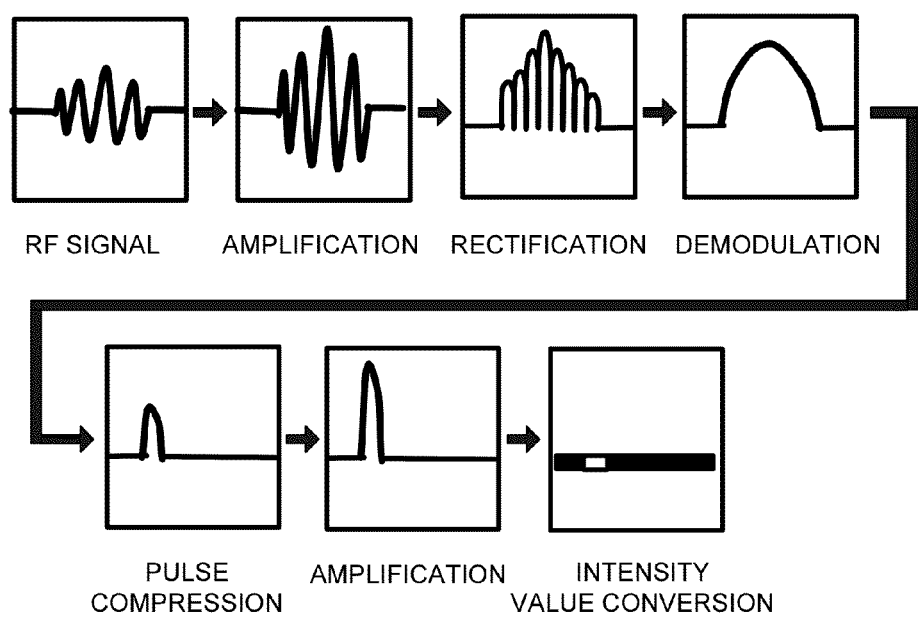

CAROTID-ARTERY-PLAQUE ULTRASOUND-IMAGING METHOD AND EVALUATING DEVICE

BACKGROUND OF THE INVENTION

1. Field of the Invention

The present invention relates to a carotid-artery-plaque ultrasound-imaging method, a carotid-artery-plaque evaluating device, a carotid-artery-plaque evaluating program, and a computer-readable storage medium that can noninvasively evaluate the properties of plaque in carotid artery by using ultrasound examination (ultrasonic pulse).

2. Description of the Related Art

Diagnosis of carotid artery plaque tissue characteristics can be used not only to evaluate stroke risk but also to predict ischemic heart disease events or to estimate therapeutic effect of lipid lowering drug for dyslipidemia. In particular, for diabetes mellitus, this diagnosis is important to estimate the prognosis or QOL of a patient.

Presently, intravascular ultrasound examination (IVUS) is used as invasive diagnosis of carotid artery plaque properties. However, the intravascular ultrasound requires catheterization in which a catheter type ultrasonic probe is inserted into a blood vessel. For this reason, the intravascular ultrasound cannot be performed for everyone. Accordingly, patients needs hospital care. As a result, it is difficult to repeatedly conduct the intravascular ultrasound.

Contrary to this, CT and MRI are used for noninvasive diagnosis of the properties. However, there is a problem with radiation exposure in the case of CT, while there is a problem that the resolution is poor in the case of MRI. In addition, CT and MRI require a large-scale device. For this reason, these noninvasive diagnosis methods cannot be conducted in a small clinic. Also, outpatients cannot freely have these noninvasive diagnosis methods.

On the other hand, a carotid artery ultrasound examination that uses echo is also used to evaluate the properties of plaque that is included in carotid artery. It is said that tissue property diagnosis can be conducted based on the echo plaque properties by the carotid artery echo test. In general, it is said that echolucent plaque near the intensity of blood shows atheroma or hematoma, that isoechoic plaque near intima media or muscle shows fibrosis, and that hyperechoic plaque near bone shows calcified lesion. Cerebrovascular infarct risk can be predicted by diagnosis of plaque based on the level of intensity. Also, risk of coronary event coronary artery can be predicted by diagnosis of plaque based on the level of echo intensity. The carotid artery echo test is a noninvasive test which outpatients can easily have.

It is considered that the echo intensity of the carotid artery plaque provides observations of diseased tissue in arteriosclerosis (Non-patent Literature 3). Generally, plaque shown by low echo intensity in echo image richly contains lipid or macrophages, and is referred to as vulnerable (unstable) plaque. On the other hand, plaque shown by high echo intensity is plaque in an advanced stage of fibrosis or calcification, and is referred to as stable plaque. FIG. 1 is a graph showing comparison of occurrence frequencies of coronary artery disorder (event) in a few tens of years between the case where plaque shown by low echo intensity is included in echo image or not. As shown in this graph, it is reported that the event more likely to occur in the case where the low echo intensity plaque is included in the carotid artery relative to the case where the high echo intensity plaque is included. That is, it is said that, if a large amount of low echo intensity plaque is included in carotid artery, this means vulnerability or instability of coronary artery (Non-patent Literature 4).

However, the carotid artery echo test is not a quantitative test but a qualitative rest. For this reason, the test observation result will vary in accordance with the skill of evaluator. Accordingly, even the same plaque may result in different diagnosis results depending on evaluator or testing devices. As a result, there is a problem that it is difficult to properly evaluate tissue characteristics of the plaque (Non-patent Literature 1). In particular, since the echo image obtained by echo devices (ultrasonic diagnostic devices) is a gray scale image, plaque properties is evaluated based on discrimination in the gray scale echo image with eyeball in the carotid artery echo test as discussed above. However, when plaque properties are classified with the naked eye based on the echo intensity levels displayed in gray scale, since the criterion of intensity level discrimination is blurry, it is difficult to quantitatively evaluate plaque properties. For example, in the case where evaluators adjust the gain, gray scale intensity level, or contrast of echo image depending on their own judgment or preferences, even when the echo images of the same patient are obtained by the same echo device, the intensity will vary in accordance with the evaluators. For this reason, it is difficult to compare images with each other. As a result, there is problems that time-variation of a patient cannot be properly checked, and that patients' cases cannot be properly compared with each other. In addition, it is difficult to evaluate plaque properties in severely calcified lesion, high grade lesion such as high grade internal carotid artery lesion, tortuous vessel, or the like.

The ultrasound intensity of the plaque can be changed in accordance with gain adjustment or image adjustment function of an echo device. For example, as shown in FIG. 17, in the case where the gain of an echo device is set to 45, 50, and 66, the echo intensity of plaque is correspondingly changed as shown in FIGS. 17A, 17B, and 17C. For this reason, even when echo images of the same subject are obtained, the echo intensity levels will be different from each other. It can be understood that difficult to quantitatively evaluate plaque properties based on echo intensity.

The gray scale in conventional echo images is represented by the intensity value of each pixel of an echo image. However, when an echo image is produced, the echo image is subjected to a number of filtering processes. The intensity value varies depending on echo devices for measuring an echo. For example, as shown in FIG. 18, an RE signal waveform of ultrasonic reflection signal (integrated backscatter: IBS), which is raw data (RAW data) obtained by an ultrasonic probe, is amplified, rectified, demodulated, subjected to pulse compression, further amplified, and converted into its intensity value. These filtering processes are differently performed depending on echo devices. Accordingly, there is a problem that even the same RF signal will be represented by different levels in gray scale in the produced echo image.

To address this issue, a method as an example for improvement of carotid artery echo test has been developed which uses hydrazide conjugate as an imaging agent, and detects and monitors the properties of plaque (Patent Literature 1). Also, improvement of echo device, improvement of imaging process, and the like can be considered. However, these improvements are not succeeded up to now.

On the other hand, IVUS that is used not in carotid artery tests but in heart coronary artery tests is an invasive method in which a catheter is inserted into a blood vessel. However, since IVUS analyses an echo wave that is directly reflected in the blood vessel, a good echo reflection wave can be obtained so that a good echo image can be produced. Form this view-point, various imaging methods have been studied (Patent Literature 2, Non-patent Literature 2).

However, if these methods are adapted to noninvasive carotid artery analysis, an echo reflection wave passes through skin or tissue. Since the echo reflection wave is analyzed, it is difficult to simply adopt these methods to noninvasive carotid artery analysis.

CITATION LIST

Patent Literature

Patent Literature 1: Patent Laid-Open Publication No. JP 2009-500,410 A
Patent Literature 2: Patent Laid-Open Publication No. JP 2009-530,068 A Non-Patent Literature Non-patent Literature 1: Neurosonology 18(2-3): 69-73, 2005
Non-patent Literature 2: Circ J. 2008, 72: 1631
Non-patent Literature 3: J Am Coll Cardiol, 2005; 46: 2022
Non-patent Literature 4: J Am Coll Cardiol, 2004; 43: 1177

The present invention is designed to solve the above problems. It is a main object of the present invention to provide a carotid-artery-plaque ultrasound-imaging method, a carotid-artery-plaque evaluating device, a carotid-artery-plaque evaluating program, and a computer-readable storage medium that can easily and visually evaluate carotid artery plaque based on a more quantitative measure.

SUMMARY OF THE INVENTION

To achieve the above object, a carotid-artery-plaque ultrasound-imaging method according to a first aspect of the present invention includes an obtaining step, a coloring step, and a displaying step. In the obtaining step, the integrated amounts per unit time of echo signals corresponding to pixels are obtained. The pixels compose an echo image of carotid artery plaque. The echo signals are obtained when the echo image is obtained by a carotid artery echo IBS method. In the coloring step, the relationship between coloring ranges and colors is referenced. The available full range of the integrated amount is previously divided into the coloring ranges. The colors are assigned to the coloring ranges. In addition, the pixels, which are included in the obtained echo image, are classified into the coloring ranges in accordance with the integrated amounts corresponding to the pixels. In addition, each of the pixels of the echo image is colored in one of the colors corresponding to the range of the each of the pixels. In the displaying step, the colored echo image is displayed on a display portion 30. According to this construction, since the echo image of the carotid artery plaque can be displayed not in conventional simple gray scale, which is not easy even for specialists to evaluate plaque properties, but in a colored image, which is easy even for tyros to evaluate plaque properties. For example, the effect of a medicine can be visually confirmed. Accordingly, it is useful to obtain patients' informed consent.

In a carotid-artery-plaque ultrasound-imaging method according to a second aspect of the present invention, the coloring ranges for classifying the integrated amount can be
a) the range of 0 to −55 dB,
b) the range of −55 to −65 dB,
c) the range of −65 to −75 dB, and
d) the range of −75 dB or less.

According to this construction, since the properties of carotid artery plaque can be easily understood by classifying the properties of carotid artery plaque into colors, it is possible to grasp even small time-variation of the plaque composition.

In a carotid-artery-plaque ultrasound-imaging method according to a third aspect of the present invention, the colors corresponding to the coloring ranges can be
a) red assigned to the range of 0 to −55 dB,
b) yellow assigned to the range of −55 to −65 dB,
c) green assigned to the range of −65 to −75 dB, and
d) blue assigned to the range of −75 dB or less.

In a carotid-artery-plaque ultrasound-imaging method according to a fourth aspect of the present invention, the echo image can include information on arteriosclerosis. According to this construction, it is possible to perform an early diagnosis of arteriosclerosis. In particular, since property variation of carotid artery plaque can be clarified, it is useful to evaluate the validity of hyperlipemia drugs for patients.

In a carotid-artery-plaque ultrasound-imaging method according to a fifth aspect of the present invention, the echo image can include information on effect of a medicine on carotid artery plaque. The effect of a medicine can be evaluated for patients who have carotid artery plaque by using this echo image of carotid artery plaque. Accordingly, the plaque stabilization of various types of medicines can be evaluated.

In a carotid-artery-plaque ultrasound-imaging method according to a sixth aspect of the present invention, the medicine can be a statin group drug.

In a carotid-artery-plaque ultrasound-imaging method according to a seventh aspect of the present invention, the statin group drug can be selected from the group consisting of atorvastatin, simvastatin, cerivastatin, pitavastatin, pravastatin, fluvastatin, mevastatin, rosuvastatin, and lovastatin.

A carotid-artery-plaque evaluating device according to an eighth aspect of the present invention includes an obtaining portion 10, a memory portion 40, a coloring portion 22, and a display portion 30. The obtaining portion 10 obtains raw signals of echo signals corresponding to reference areas that compose an echo image of carotid artery plaque. The echo signals are obtained when the echo image is obtained by a carotid artery echo IBS method. The memory portion 40 stores the relationship between coloring ranges and colors. The available full range of the raw signal is previously divided into the coloring ranges. The colors are assigned to the coloring ranges. The coloring portion 22 classifies the reference areas, which are included in the echo image, into the coloring ranges in accordance with the raw signals corresponding to the reference areas by referencing the memory portion 40. The coloring portion 22 colors each of the reference areas of the echo image in one of the colors corresponding to the raw signal of the each of the reference areas. The display portion 30 displays the echo image colored by the coloring portion 22. The memory portion 40 stores the relationship between coloring ranges and colors in which the coloring ranges corresponding to high intensity and low intensity among the coloring ranges for classifying the raw signal are colored in red, and green or blue. According to this construction, since the echo image of the carotid artery plaque can be colored to be easily distinguished when displayed, it is possible to easily grasp even small time-variation. In addition, it is possible to early detect vascular disorder based on the carotid artery echo image analysis.

In a carotid-artery-plaque evaluating device according to a ninth aspect of the present invention, the reference areas, which compose the echo image, can be pixels that compose the echo image.

In a carotid-artery-plaque evaluating device according to a tenth aspect of the present invention, the raw signals can be echo signals that are obtained by a carotid artery echo IBS method.

In a carotid-artery-plaque evaluating device according to an eleventh aspect of the present invention, the raw signal can be corrected with reference to the value of a specific part in the echo image. The coloring portion 22 can color the echo image based the corrected raw signal by referencing the relationship, which is stored in the memory portion 40, so that the colored echo image is displayed on the display portion 30. According to this construction, since a specific part is commonly selected in the echo image, the raw signal can be corrected with reference to the specific part as common reference. Accordingly, different echo images can be commonly classified in colors. Therefore, it is possible to provide more stable diagnosis with less variation.

In a carotid-artery-plaque evaluating device according to a twelfth aspect of the present invention, the raw signal can be corrected so that the value corresponding a blood part in the echo image is set to the minimum of the available full range of the raw signal. According to this construction, since the raw signal of the echo image corresponding to the blood part can be commonly used as the minimum value, it is possible to reduce variation between echo images.

In a carotid-artery-plaque evaluating device according to a thirteenth aspect of the present invention, the raw signal can be corrected so that the value corresponding a blood vessel part in the echo image is set to the maximum of the available full range of the raw signal. According to this construction, since the raw signal of the echo image corresponding to the blood vessel part can be commonly used as the maximum value, it is possible to reduce variation between echo images.

In a carotid-artery-plaque evaluating device according to a fourteenth aspect of the present invention, the raw signals can be the integrated amounts per unit time of echo signals that are obtained when the echo image is obtained.

In a carotid-artery-plaque evaluating device according to a fifteenth aspect of the present invention, the display portion 30 can display the integrated amounts in histogram form. According to this construction, it is possible to easily and visually grasp the integrated amounts based on the histogram.

In a carotid-artery-plaque evaluating device according to a sixteenth aspect of the present invention, an operation portion 50 can be further provided capable of setting any point on the echo image that is displayed on the display portion 30. In the case where the echo image is displayed on the display portion 30, when a blood vessel lumen is set by the operation portion 50, the integrated amount corresponding to the position of the blood vessel lumen can be corrected to the minimum of the integrated amount. According to this construction, since the integrated amounts can be corrected based on the integrated amount corresponding to blood in the blood vessel lumen where plaque is not present, it is possible to evaluate the properties of carotid artery plaque with small variation between patients.

In a carotid-artery-plaque evaluating device according to a seventeenth aspect of the present invention, an operation portion 50 can be further provided capable of setting any point on the echo image that is displayed on the display portion 30. In the case where the echo image is displayed on the display portion 30, when adventitia is set by the operation portion 50, the integrated amount corresponding to the position of the adventitia can be corrected to the maximum of the integrated amount. According to this construction, since the integrated amounts can be corrected based on the integrated amount corresponding to tissue in the adventitia where plaque is not present, it is possible to evaluate the properties of carotid artery plaque with small variation between patients.

In a carotid-artery-plaque evaluating device according to an eighteenth aspect of the present invention, an area-setting portion can be further provided capable of setting an area of carotid artery plaque on the echo image that is displayed on the display portion 30. The coloring portion 22 can color the carotid artery plaque based on the specified area RI that is set by the area-setting portion when the carotid artery plaque is displayed. According to this construction, since the area of carotid artery plaque to be displayed in color can be set, it is possible to provide visible display where only required parts are displayed in color.

In a carotid-artery-plaque evaluating device according to a nineteenth aspect of the present invention, a plurality of specified areas RI can be set by the area-setting portion, and identification numbers can be assigned to the specified areas RI. According to this construction, since a plurality of areas can be distinguished based on the identification numbers, users can grasp the plurality of areas without confusion.

In a carotid-artery-plaque evaluating device according to a twenty aspect of the present invention, the occupancy ratio between colored areas that are colored by the coloring portion 22 can be displayed in graph form on the display portion 30. According to this construction, as for types of carotid artery plaque, for example, calcified plaque, high fibrous plaque, fibrous plaque, and lipid-rich plaque can be displayed in red, yellow, green, and blue, respectively. Accordingly, the ratio between them can be visually grasped. As a result, it is possible to quantitatively evaluate the properties of plaque.

In a carotid-artery-plaque evaluating device according to a twenty-first aspect of the present invention, the display portion 30 can display divided areas that can display two echo images on the screen of the display portion. One of divided display areas can display an uncolored echo image, while another divided display area can display the colored echo image that corresponds to the uncolored echo image and is colored by the coloring portion 22. According to this construction, a colored image that shows carotid artery plaque in color can be displayed for comparison with the uncolored image corresponding to the colored image. Alternatively, time variation can be grasped on one screen. Therefore, it is possible to provide an improved visible display.

In a carotid-artery-plaque evaluating device according to a twenty-second aspect of the present invention, the obtaining portion 10 can be a reading portion that can read a memory medium that stores the raw signals of the echo image obtained by an external ultrasonic probe. According to this construction, when an echo image obtained by an echo device can be read into the evaluating device, the properties of carotid artery plaque can be evaluated. As a result, the evaluating device can use RAW data output that can be provided by existing echo devices in diagnosis.

In a carotid-artery-plaque evaluating device according to a twenty-third aspect of the present invention, the obtaining portion 10 can be an ultrasonic probe that can obtain an echo image 10B. According to this construction, the carotid artery plaque diagnostic function is included into an echo device itself. Accordingly, the echo device can color an echo image obtained by the echo device on the display portion.

A carotid-artery-plaque evaluating program according to a twenty-fourth aspect of the present invention causes a computer to realize an obtaining function, a table-storing function, a coloring function, and a display function. The obtaining function obtains raw signals of echo signals corresponding to areas that compose an echo image of carotid artery plaque. The echo signals are obtained when the echo image is obtained by a carotid artery echo IBS method. The table-storing function stores the relationship between coloring ranges and colors. The available full range of the raw signal is previously divided into the coloring ranges. The colors are assigned to the coloring ranges. The coloring function classifies the areas, which are included in the echo image, into the coloring ranges in accordance with the raw signals corresponding to the areas by referencing the table-storing function, and colors each of the areas of the echo image in one of the colors corresponding to the raw signal of the each of the areas. The display function displays the echo image colored by the coloring function. According to this construction, since the echo image of the carotid artery plaque can be displayed not in conventional simple gray scale, which is not easy even for specialists to evaluate plaque properties, but in a colored image, which is easy even for tyros to evaluate plaque properties. For example, the effect of a medicine can be visually confirmed. Accordingly, it is useful to obtain patients' informed consent.

A computer-readable storage medium according to a twenty-fifth aspect of the present invention has the aforementioned program. The storage medium can be CD-ROM, CD-R, CD-RW, flexible disk, magnetic tape, MO, DVD-ROM, DVD-RAM, DVD-R, DVD+R, DVD-RW, DVD+RW, Blu-ray, magnetic disk such as HD DVD (AOD), optical disc, magneto-optical disk, semiconductor memory, other medium that can store the program. The program can be distributed in a form stored in the storage medium, and be also distributed through network such as the Internet (downloaded). The storage medium can include a device that can store the program, for example, a general-purpose device or special-purpose device on which the aforementioned program is installed in a form of executable software, firmware on the like. Processes or functions included in the program can be executed by the program software that can be executed by a computer. The processes of parts can be realized by hardware such as certain gate array (FPGA, ASIC), or a form of combination of program software and partial hardware module that realizes parts of elements of hardware.

BRIEF DESCRIPTION OF THE DRAWINGS

FIG. 2.

FIG. 3: FIG. 3A shows an echo image of carotid artery plaque, and FIG. 3B shows a colored image corresponding to the image shown in FIG. 3A.

FIG. 4: FIG. 4A shows an echo image of carotid artery plaque, and FIG. 4B shows a colored image corresponding to the image shown in FIG. 4A.

FIG. 5: FIG. 5A shows an echo image of carotid artery plaque, and FIG. 5B shows a colored image corresponding to the image shown in FIG. 5A.

FIG. 6: FIG. 6A shows a colored image and specific data in the case where the intensity distribution of plaque corresponds to hypoechoic plaque, FIG. 6B shows a colored image and specific data in the case where the intensity distribution corresponds to isoechoic plaque, and FIG. 6C shows a colored image and specific data in the case where the intensity distribution corresponds to hyperechoic plaque.

FIG. 7.

FIG. 8.

FIG. 9: FIG. 9A shows an echo image before CEA, FIG. 9B shows a colored image corresponding to FIG. 9A, and FIG. 9C shows an image corresponding to FIGS. 9A and 9B with a part to be removed being colored by HE staining.

FIG. 10: FIGS. 10A and 10B show histograms of IB value of blood vessel lumen before and after correction, respectively, and FIGS. 10C and 10D show histograms of IB value of adventitia before and after correction, respectively.

FIG. 11.

FIG. 12.

FIG. 13.

FIG. 14.

FIG. 15.

FIG. 16.

FIGS. 17A, 17B, and 17C show echo images in the case where gains of the echo device are set to 45, 50, and 66, respectively.

FIG. 18: Schematic view showing processes in which an RF signal waveform of echo signal is amplified, rectified, demodulated, subjected to pulse compression, further amplified, and converted into its intensity value.

FIG. 25.

FIG. 26.

DETAILED DESCRIPTION OF THE EMBODIMENT(S)

Figure 1:
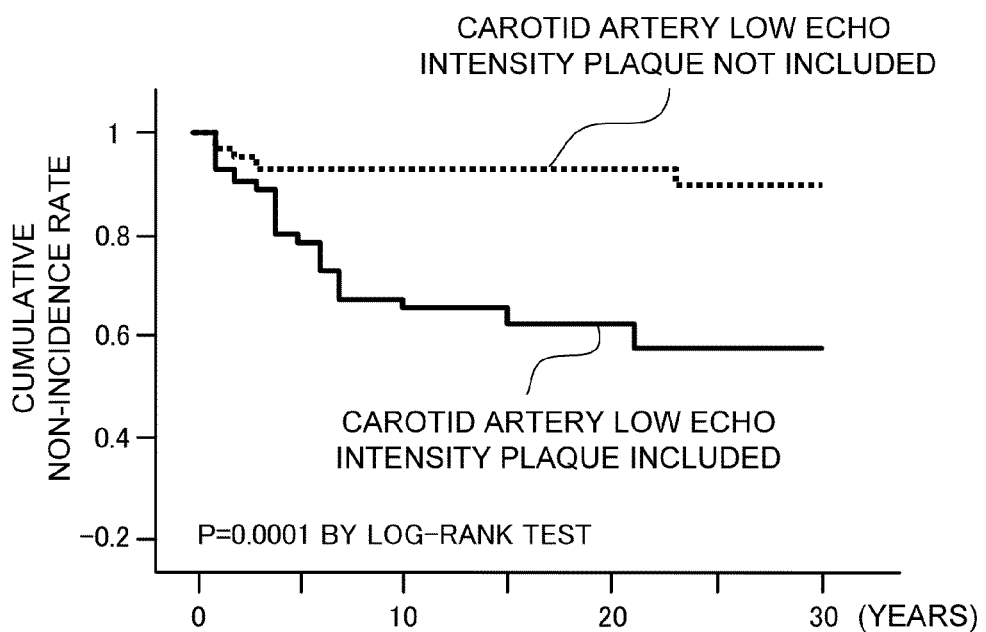
FIG. 1: Graph showing the relationship between the properties of plaque evaluated by carotid artery echo and coronary artery infarct.

The following description will describe embodiments according to the present invention with reference to the drawings. It should be appreciated, however, that the embodiments described below are illustrations of a carotid-artery-plaque ultrasound-imaging method, a carotid-artery-plaque evaluating device, a carotid-artery-plaque evaluating program, and a computer-readable storage medium to give a concrete form to technical ideas of the invention, and a carotid-artery-plaque ultrasound-imaging method, a carotid-artery-plaque evaluating device, a carotid-artery-plaque evaluating program, and a computer-readable storage medium of the invention are not specifically limited to description below. Furthermore, it should be appreciated that the members shown in claims attached hereto are not specifically limited to members in the embodiments. Unless otherwise specified, any dimensions, materials, shapes and relative arrangements of the parts described in the embodiments are given as an example and not as a limitation. Additionally, the sizes and the positional relationships of the members in each of drawings are occasionally shown larger exaggeratingly for ease of explanation. Members same as or similar to those of this invention are attached with the same designation and the same reference signs, and their description is omitted. In addition, a plurality of structural elements of the present invention may be configured as a single part that serves the purpose of a plurality of elements, on the other hand, a single structural element may be configured as a plurality of parts that serve the purpose of a single element.

A carotid artery plaque evaluating device and evaluating program that are used in embodiments of the present invention can be electrically, magnetically or optically connected to and communicate with a computer for operation, control, display and other processes, a printer, an external storage or other peripheral device through serial connection such as IEEE1394, RS-232x, RS-422, RS-423, RS-485 and USB, parallel connection, or a network such as 10BASE-T, 100BASE-TX and 1000BASE-T. The connection is not limited to the physical connection using cables. The connection can be wireless connection using electric waves, infrared rays, optical communications or the like such as wireless LAN (e.g., IEEE802.1x), and Bluetooth (registered trademark). A memory card, a magnetic disk, an optical disk, a magneto-optical disk, a semiconductor memory, and the like can be used as a storage medium for data exchange, setting retention, and the like. In this specification, the carotid artery plaque evaluating device and evaluating program refer not only to an evaluating device itself but also to an evaluating system that includes a computer and peripheral devices such as external storage in addition to this evaluating device.

In the specification, the carotid artery plaque evaluating device and evaluating program are not limited to a system itself that evaluates the carotid artery plaque. Also, the carotid artery plaque evaluating device and evaluating program are not limited to a device or a method that performs input/output, display, calculation, communication, and the other processes relating evaluation of carotid artery plaque by using hardware. A device and method that realize the processes by using software are also included within the scope of the present invention. For example, the carotid artery plaque evaluating device and evaluating program according to the present invention include a device or system having a general-purpose circuit or computer that is incorporated with software, program, plug-in, object, library, applet, compiler, module, macro that can be executed in a particular program so as to perform image processing or processing relating to image processing. In this specification, a computer includes a workstation, a terminal, a portable electronic device, and other electron devices as well as general-purpose device and special-purpose electronic computers. In this specification, the program is not limited to a program that can be used itself alone, but can be a form that functions as a part of a particular computer program, software, service or the like, a form that functions after downloaded when necessary, a form that is provided as service in environment of OS or the like, a form that stays resident in environment, or a form that is executed in the background, or other support program.

In this specification, a "carotid artery plaque property determining method" refers to a method that colors and visualizes plaque by using data processing based on the IBS method. The "IBS (integrated backscatter) method" analyzes reflection signals when an echo is measured. That is, BS (backscatter) signals that are reflected by a reflection subject sufficiently smaller than the wavelength of the echo include very small ultrasonic waves from the inside of tissue. Accordingly, the signals are integrated so that the integrated amounts per unit time are obtained. As a result, data including information on the properties of tissue can be obtained (The Lipid Vol. 18, 53 (2007)).

In this specification, "echo intensity" be pursuant to the guidelines for echo diagnosis in Japan, and can be classified into three of hypoechoic, isoechoic, and hyperechoic classes. According to the guidelines, the hypoechoic class (plaque) is an intensity range that is not easily seen only in B-mode. The isoechoic class (plaque) is an intensity range that is close to the intensity of muscle or intima media. The hyperechoic class (plaque) is an intensity range that is similar to the intensity of bone. It is said that the echo intensity has relationship with histopathological properties of the plaque. The hypoechoic plaque corresponds to atheroma, intraplaque hemorrhage, or lipid. The isoechoic plaque corresponds to fibrous lesions. The hyperechoic plaque corresponds to calcified lesions. In the specification, the echo intensity is classified into four ranges according to the data of the IBS method, and displayed in colors so that the properties of the plaque can be visible.

(Carotid Artery Plaque Evaluating Device)

Figure 19:
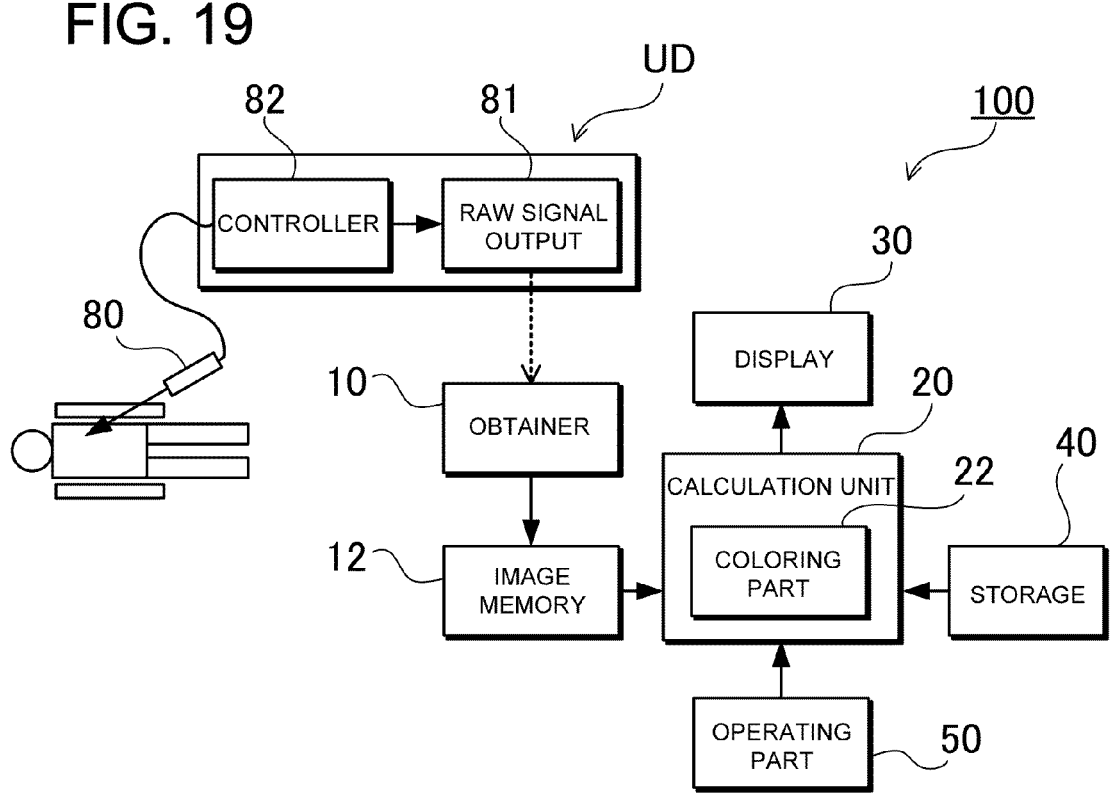
FIG. 19: Block diagram showing a carotid artery plaque evaluating device.
Figure 20:
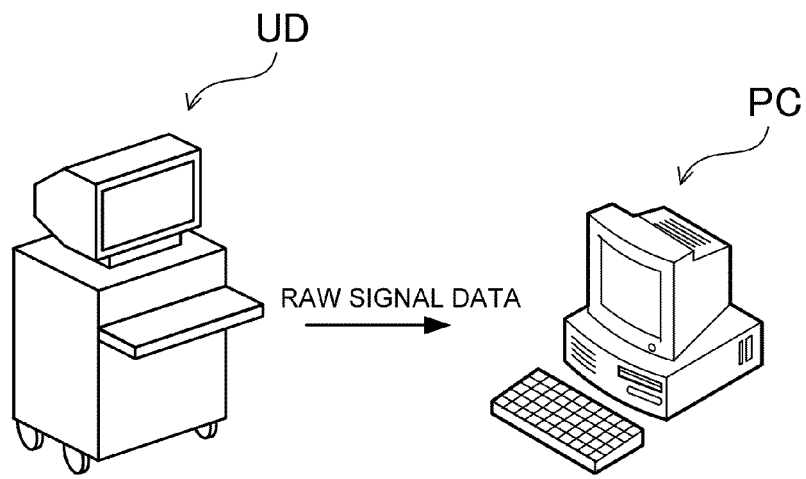
FIG. 20: Schematic view showing the evaluating device and the echo device with raw signals of the echo image obtained by the echo device being read into the evaluating device.

FIG. 19 is a block diagram showing a carotid artery plaque evaluating device. This illustrated evaluating device 100 includes an obtaining portion 10, a calculation portion 20, a display portion 30, a memory portion 40, an operation portion 50, and an image memory 12. As shown in FIG. 20, the evaluating device 100 is a system that includes the obtaining portion 10 that can read raw signals of ultrasonic reflection signals (echo signals) that is used as original data of an echo image that is obtained by an separately prepared echo device UD (ultrasonic diagnostic device), and the display portion 30 that can display a colored image part that is colored by the calculation portion 20 in accordance with the properties of plaque on this echo image.

A computer in which a carotid artery plaque evaluating program (discussed later) is installed is used as the carotid artery plaque evaluating device 100. However, the carotid artery plaque evaluating device is not limited to this construction. For example, the evaluating device can be constructed of special-purpose hardware. Alternatively, the evaluating function of the carotid artery program can be installed in the echo device itself. In this case, the properties of plaque can be visually grasped in real time based on the colored image when the echo image is displayed on the echo device.

In the evaluating device 100 shown in FIG. 19, the obtaining portion 10 obtains the raw signals of echo signals corresponding to reference areas that compose an echo image of carotid artery plaque. The echo signals are obtained when the echo image is obtained. It is preferable that the raw signals be RF signals of echo signals. In other words, it is preferable that the raw signals be raw data (RAW data) before various filtering processes (for example, smoothing, noise rejection, edge enhancement, gray scale transformation enhancement, histogram transformation enhancement, etc.) performed by the echo device, or the like. The signal intensities in raw data are independent from variation between echo devices or settings. Accordingly, the signal intensities in raw data reflect the original properties of living body tissue. As a result, the signal intensities can provide quantitative evaluation.

RF signals that are obtained by the ultrasound backscattering (IBS: integrated backscatter) method is used as the raw signals. Accordingly, the evaluation cannot be affected by variation between diagnostic devices or device setting conditions such as in the case of GSM (gray-scale median). As a result, it is possible to provide more quantitative evaluation based on a more quantitative measure than the conventional qualitative evaluation based on the classes in an echo image such as hypoechoic, isoechoic, and hyperechoic classes.

The raw signal is the integrated amount per unit time of an echo signal (IB value). For this reason, it is necessary for the echo device UD that obtains echo signals to deal with the IB value output. For example, the echo device UD includes a raw signal output portion 81 that can output the raw signals before signal processing as they are, or has a conversion function for inversely transforming data after the signal processing to the raw signals. The echo device UD shown in FIG. 19 includes an ultrasonic probe 80 that obtains an echo image, and a controller 82 that controls the echo device UD, and the raw signal output portion 81. In addition, the raw signal output portion 81 preferably includes a function that provides the raw signals to the evaluating device 100, for example, a function that writes the data in a memory medium, or a communication function that outputs the raw signals to the evaluating device by wire or wirelessly according to data communications. In the following examples, IB images are shown as the echo images. The echo image is produced based on the IB values, and is formed on the image memory 12.

(Obtaining Portion 10)

In the evaluating device shown in FIG. 20, the obtaining portion 10 is a reading portion that can read a memory medium that stores the raw signals of the echo image obtained by the echo device UD. For example, the IB signals obtained by the echo device UD can be stored in a semiconductor memory such as USB memory and SD card (trade name). The obtaining portion includes an interface that can connect this memory to the evaluating device 100, and reads the data. The reading device can be a card reader based on the semiconductor memory standards, or a disk drive. In the case of USB memory, or the like, the reading device can be a USB port, or the like. According to this construction, if an existing echo device has a function that can write the raw signals such as IB values, the existing echo device can use this. Accordingly, the present invention can be easily adopted to existing equipment without adding a special device to the existing echo device and remodeling the existing echo device.

Alternatively, the raw signals can be directly transmitted from the echo device to the evaluating device by wire or wirelessly (WiFi, Bluetooth (registered trademark), infrared rays, optical communications, etc.) as discussed above without using the semiconductor memory.

(Calculation Portion 20)

It is preferable that the reference areas, which compose the echo image, be pixels. The pixels can be classified in colors in accordance with the IB values of the pixels. This coloring process is performed by the calculation portion 20. The calculation portion 20 includes a coloring portion 22. The memory portion 40 is connected to the calculation portion 20. The memory portion stores the relationship between coloring ranges and colors. The available full range of the raw signal is previously divided into the coloring ranges. The colors are assigned to the ranges. The coloring portion 22 classifies the reference areas, which are included in the echo image, into the coloring ranges in accordance with the raw signals corresponding to the reference areas by referencing the memory portion 40, and colors each of the reference areas of the echo image in one of the colors corresponding to the raw signal of the each of the reference areas.

The memory portion 40 can be a storage device such as ROM. The memory portion 40 stores an assignment table representing the relationship between the value of raw signals and colors. For example, IB values are classified into the following four ranges of a to d. Different colors are assigned to the ranges.

a) 0 to −55 dB: Red (indication of calcified plaque)
b) −55 to −65 dB: Yellow (indication of high fibrous plaque)
c) −65 to −75 dB: Green (indication of fibrous plaque)
d) −75 dB or less: Blue (indication of lipid-rich plaque)

Colors are not specifically limited as long as they can be easily distinguished from each other. In this embodiment, red, yellow, green, and blue are assigned to the ranges in this order from highest intensity range.

The coloring portion 22 determines the colors of IB value ranges according to this relationship, and colors the pixels of the positions in the echo image corresponding to the IB value ranges in the assigned colors. Not the whole echo image, but a specified area RI of the echo image is subjected to the coloring process. That is, when an area corresponding to the plaque is previously set as the specified area RI, only this area can be subjected to the coloring processes and displayed in colors. Accordingly, users can see colored image in which only a required part, i.e., a part corresponding to plaque is classified by colors. Therefore, it is possible to provide an improved visible display.

The operation portion 50 is a member that allows users to set a specified area RI. A pointing device such as mouse can be used as the operation portion. The specified area RI can be set by specifying a particular shape such as rectangle or circle area by using the mouse. Alternatively, the specified area RI can be set by surrounding a part with a free form line. Alternatively, the specified area RI can be set by image processing such as edge detection. Any suitable area-setting methods can be used for setting the specified area RI.

The echo image and the colored image can be displayed on the display portion. The display portion can be a monitor such as liquid crystal display, CRT, organic electroluminescence.

Figure 21:
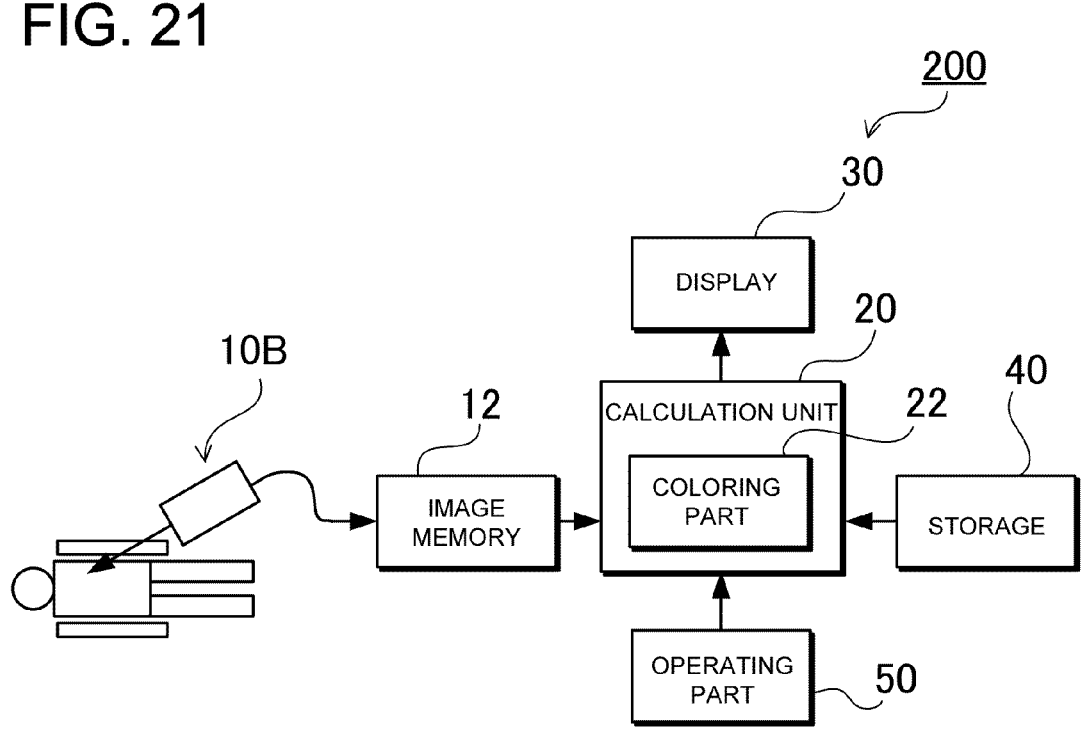
FIG. 21: Block diagram showing the evaluating device according to a modified embodiment that includes an echo image obtaining function.

However, the carotid artery plaque evaluating device is not limited to the aforementioned construction. For example, the display portion can be incorporated into the echo device itself. For example, an evaluating device 200 shown in FIG. 21 is not separately constructed from the echo device, but is constructed integrally with the echo device. In this case, the ultrasonic probe that obtains an echo image can be used as an obtaining portion 10B. According to this construction, after the echo image is obtained by the evaluating device 200, which also serves as the echo device, the properties of plaque can be visually grasped in real time based on the colored image when the echo image is displayed on the display portion 30.

(Carotid Artery Plaque Evaluating Program)

Figure 22:
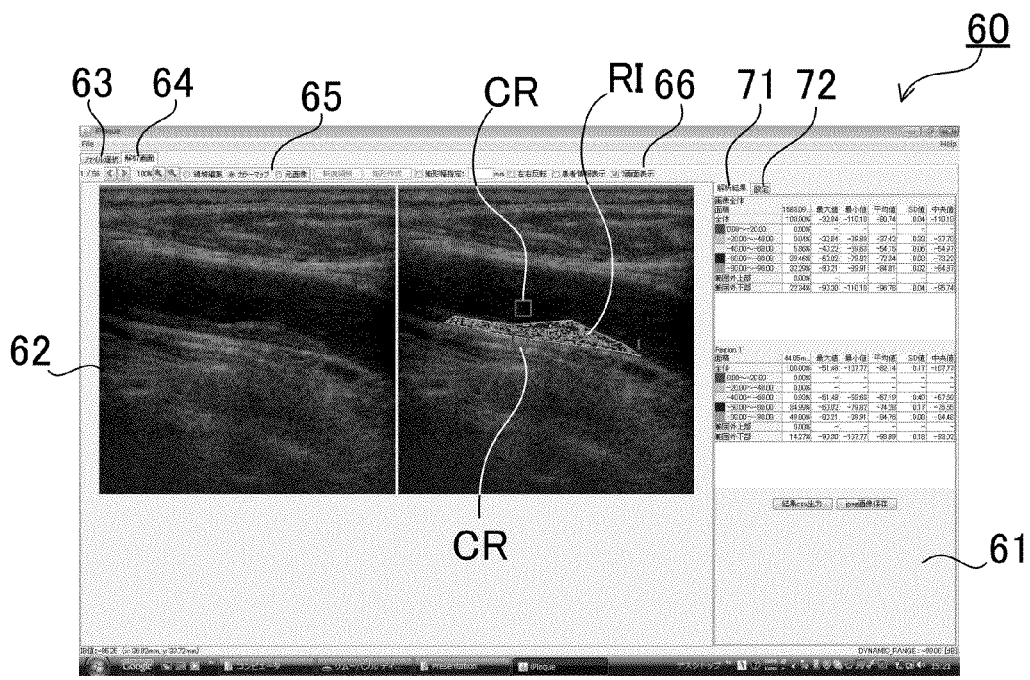
FIG. 22: Image showing the user interface display of a carotid artery plaque evaluating program.
Figure 23:
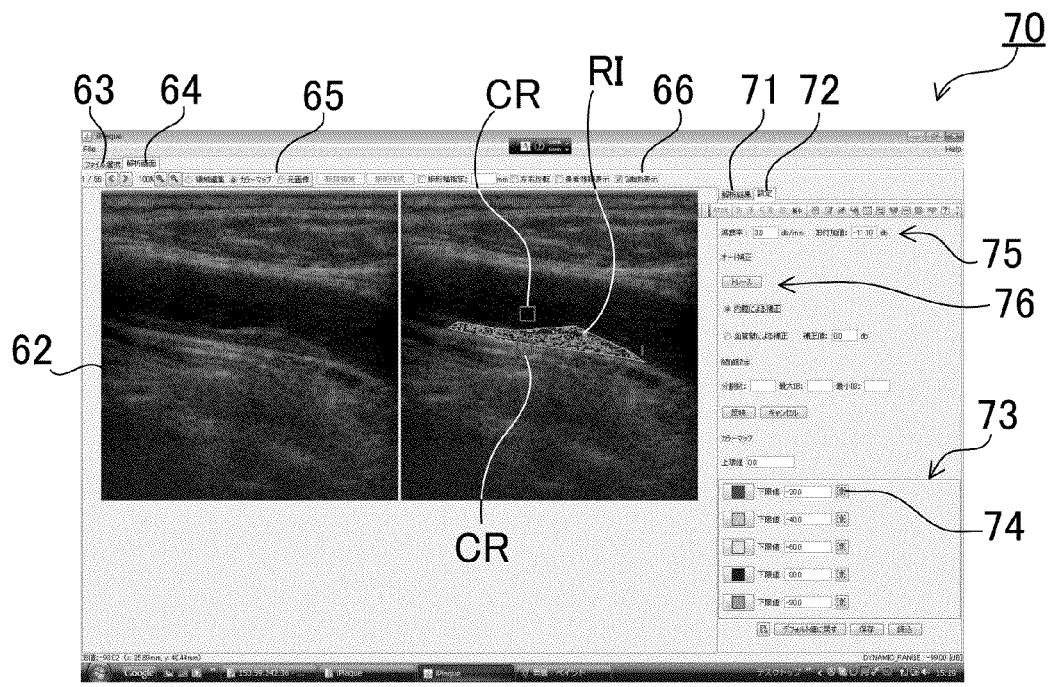
FIG. 23: Image showing the display after the "settings" tab is selected on the display shown in FIG. 22.
Figure 24:
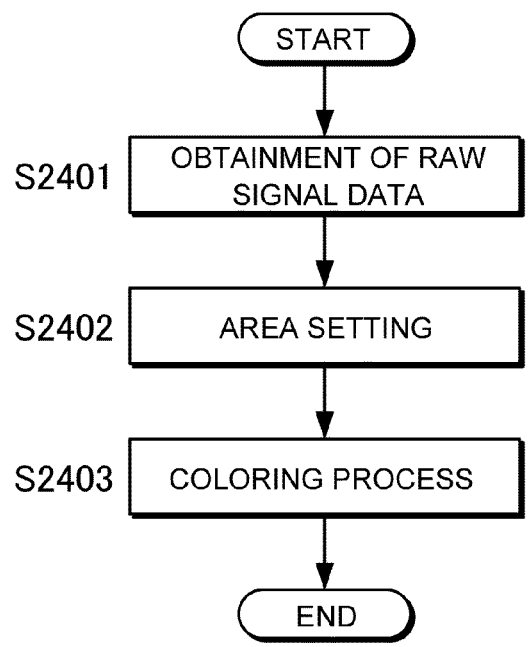
FIG. 24: Flowchart showing the procedure of evaluating program for coloring an echo image.

FIGS. 22 and 23 are images showing the user interface displays of a carotid artery plaque evaluating program. The illustrated evaluation program is executed on a computer PC shown in FIG. 20. Thus, the computer PC shown in FIG. 20 on which the evaluation program is installed composes the carotid artery plaque evaluating device. A user interface display 60 includes image display and operation areas 62 and 61 that are arranged on the left and right sides, respectively. The image display area 62 displays echo images. The operation area 61 displays various settings and the analysis result. The evaluation program is an imaging application that colors an echo image. The following description will describe the procedure for coloring an echo image with reference to a flowchart of FIG. 24.

(Step S2401: Obtainment of Raw Signal Data)

First, in Step S2401, raw signal data is obtained. Specifically, a "file selection" tab 63 that is arranged in the image display area 62 is selected so that the raw signal of the echo image is inputted. In this embodiment, the image data of the echo image to be obtained is selected from an external storage such as semiconductor memory, or a data file that is previously stored in the evaluating device.

(Step S2402: Selection of Specified Area RI)

After the image data is selected, the image display area 62 is switched to an "analysis display" tab 64 so that the image data of the echo image is displayed. After that, users operate the mouse or the like as are the operation portions 50, and set an area to be subjected to the coloring process (Step S2402). In this embodiment, a line is continuously drawn and formed in a closed area with the mouse for setting carotid artery plaque so that the specified area RI can be defined. In this case, a plurality of specified areas RI can be set. In addition, identification numbers are assigned to the specified areas RI in the selected order. Specifically, the identification number "1" is displayed on upper right part of the specified area RI on the image display area 62. For example, different colors are assigned to frames that surround the areas, while identification information corresponding to each of the frames is displayed in the same color as the each of the frames. As a result, it is possible to easily and visually distinguish the plurality of specified areas from each other. An area to be colored can be automatically specified by image processing without users' setting of a specified area. Alternatively, the whole echo image can be subjected to the coloring process. In this case, needless to say, it is possible to omit specifying a specified area.

(Step S2403: Coloring Process)

After the specified area RI is specified, the coloring process is performed by the coloring portion 22 (Step S2403). The coloring process is activated by a display switching portion. In this embodiment, a switching radio button 65 is arranged in the tool bar as the display switching portion. The switching radio button 65 can switch from "area edit" to "color map". Accordingly, as shown in FIGS. 22 and 23, after subjected to the coloring process, the colored image in the specified area RI is displayed on the image display area 62. When the switching radio button 65 is switched to the "original image", the display mode of the image display area 62 can be switched to the display of the original image before the coloring process. When the switching radio button 65 is switched to the "area edit", the display mode of the image display area 62 can be switched to the selection display of the specified area RI. Although the exemplary construction has been described, a special-purpose activation button can be provided to be pressed for activation of the coloring process.

(Display Area Dividing Portion)

The image display area 62 shown in FIGS. 22 and 23 is divided into two divided display areas. An original image and a colored image of the original echo image are displayed on the left and right sides, respectively. According to this construction, it is possible to easily compare colored parts with uncolored parts. As a result, since users can confirm the coloring appropriateness or the correspondence between the original image and colored image, it is possible to evaluate the properties of the carotid artery plaque. The display can be switched to the two-area display mode by using a display area dividing portion. In this embodiment, a "two-area display mode" check box 66 is arranged in the tool bar. When the check box 66 is checked, the display is switched to the two-area display mode. When the check box 66 is unchecked, the display is switched to the single-area display mode so that the echo image is displayed larger in the whole image display area 62.

Also, as shown in FIG. 22, when an "analysis result" tab 71 is selected, the areas of colored parts corresponding to the coloring areas are indicated in the operation area 61. In this case, only one specified area RI is specified. The distribution of the coloring ranges of the specified area 1 is displayed on the middle part of the operation area 61, and the distribution of the coloring ranges of the whole image is displayed on the upper part of the operation area 61. Although the distribution is displayed in a tabular form in this case, the distribution can be displayed in a circle graph as discussed later shown in FIG. 7 or the like. Alternatively, the IB values can be displayed in histogram as shown in FIG. 10 or the like. As discussed above, the display form can be suitably changed. As a result, it is possible to evaluate the carotid artery plaque from various viewpoints.

(Setting Display 70)

When a "setting" tab 72 is selected in the operation area 61, as shown in FIG. 23, the display is switched to a setting display 70. In this display, coloring range settings and correction can be made. As shown in FIG. 23, a color assigning portion 73 is arranged in the lower part of the operation area 61, and indicates color assignment to the coloring ranges. In this case, red, orange, yellow, blue, and green are assigned to the ranges of 0 to −20 dB, −20 to −40 dB, −40 to −60, −60 to −80 dB, and −80 dB or less, respectively. The colors are assigned according to the color assignment that is used in the coronary artery indication. However, needless to say, any colors may be assigned to the ranges. The thresholds upper and lower limits of the coloring ranges are set to default values. However, users may set the thresholds to any values. For example, color selecting buttons 74 are arranged on the right sides of the coloring ranges. When one of the color selecting buttons 74 is clicked, a rectangle color assignment area CR is indicated in the image display area 62. The thresholds are automatically adjusted so that the color that is selected by the one of the color selecting buttons is assigned to the area that is defined by color assignment area CR. According to this construction, users can directly select an area to be colored in the echo image, and a color to be assigned to the selected area. In this case, for example, the color assignment area CR corresponding to the coloring range to be assigned to red is indicated in red, while the color assignment area CR corresponding to the coloring range to be assigned to blue is indicated in blue. According to this construction, users can visually distinguish a plurality of color assignment areas from each other. Thus, the relationship between the raw signals and colors can be set or modified by the coloring ranges that are specified by the color assigning portion 73, and is stored in the memory portion 40.

Furthermore, the adjustment boxes 75 are arranged in the upper part of the operation area 61. The adjustment boxes 75 serve as an attenuation adjusting portion that correcting the attenuation of ultrasonic that is produced in accordance with the depth. The attenuation rate and IB addition value can be set in the adjustment boxes 75.

(Correction Portion)

In addition, the evaluating device includes a correction portion that corrects the assignment to the raw signals by using the raw signals of blood vessel lumen or adventitia. The correction is performed based on the raw signals of a blood part or a blood vessel part. For example, the correction is performed based on the integrated amount of a part corresponding to a blood part in blood vessel lumen in the echo image so that this integrated amount is defined as the minimum. Alternatively, the correction is performed based on the integrated amount of a part corresponding to adventitia in the echo image so that this integrated amount is defined as the maximum. According to the correction, it is possible to reduce variation between echo images, for example, variation between patients or variation between images of the same patient that are obtained on different dates. In general, the pixel value of blood is likely to be the lowest (for example, black), while the pixel value of blood vessel is likely to be the highest (for example, white). For this reason, the aforementioned common measure is defined so that measurement variation is suppressed. As a result, it is possible to obtain echo images base on the common measure. In the correction, the raw signals are changed based on the reference value. Alternatively, the raw signals may be unchanged, but the coloring ranges may be changed based on the reference value. Also, in this case, similar effects can be obtained.

Specifically, in the evaluating program shown in FIGS. 22 and 23, the correction radio buttons 76 are provided as correction function. "Correction based on lumen" or "correction based on blood vessel wall" can be alternatively selected by the correction radio buttons 76. For example, when "correction based on lumen" is selected by the correction radio button 76, a rectangle lumen correction area is displayed in the image display area 62. The area specified by this lumen correction area is determined as lumen. Accordingly, the correction is performed so that the IB value of this area is defined as the minimum. Since blood is present in a lumen, it is considered that a part of the lumen in the echo image is displayed in black. The IB value is corrected so that this part becomes black. As a result, it is possible reduce variation of the IB value distributions between patients subjected to the measurement. Similarly, when "correction based on blood vessel wall" is selected by the correction radio button 76, a rectangle blood vessel correction area is displayed. The area specified by this blood vessel correction area is determined as blood vessel. Accordingly, the correction is performed so that the IB value of this area is defined as the maximum. It is considered that a part of the adventitia in the echo image is displayed in white. The IB value is corrected so that this part becomes white. As a result, it is also possible reduce measurement variation. Since the IB value is adjusted based on the parts which do not correspond to plaque and can be expected to be stably measurement, it is possible to more reliable measurement.

Figure 25A:
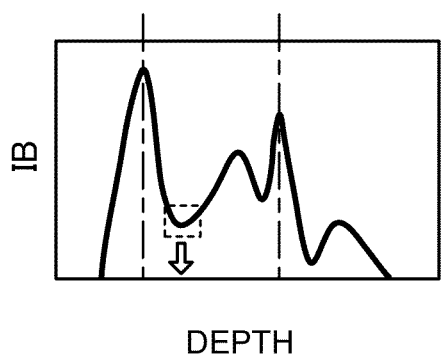
FIGS. 25A and 25B shows histograms of IB value of blood vessel lumen before and after shift correction, respectively.

FIGS. 25A to 26B are graphs showing correction of IB value. These graphs show histograms showing distribution of IB values of the pixels included in the echo image at each depth. FIGS. 25A and 25B show correction of IB value of blood vessel lumen. FIG. 25A is the histogram of the original IB value, while FIG. 25B is the histogram of IB value after correction. In these histograms, it is considered that the two peaks shown by the single-dot-dashed lines indicate the positions of blood vessel outer walls, that a part between the blood vessel outer walls indicates a blood vessel lumen, and that a relative minimum indicates blood, in particular. Correction is performed so that the relative minimum is defined as the minimum of IB value. Thus, the reference value of IB value can be defined commonly with echo images (blood). Accordingly, it is possible to reduce measurement variation between echo images or variation between objects subjected to measurement. As a result, it is possible to provide diagnosis based on the common reference values. A part shown by the rectangle line in FIG. 25A corresponding to the relative minimum as the blood vessel lumen is specified. The waveform of IB value is corrected so that the value of the blood vessel lumen part is defined as the minimum. Thus, the waveform of IB value is shifted as shown in FIG. 25B. The blood part can be displayed in the same color in the echo image that is represented by the IB values after correction. The echo image after the IB value correction is subjected to the coloring process. Accordingly, it is possible to provide diagnosis of plaque parts based on the common reference. As a result, the echo images can be easily compared with each other.

Figure 26A:
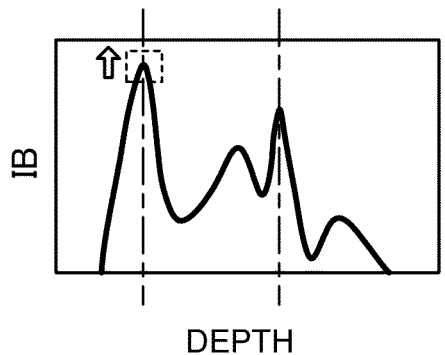
FIGS. 26A and 26B show histograms of IB value of adventitia before and after shift correction, respectively.
Figure 26B:
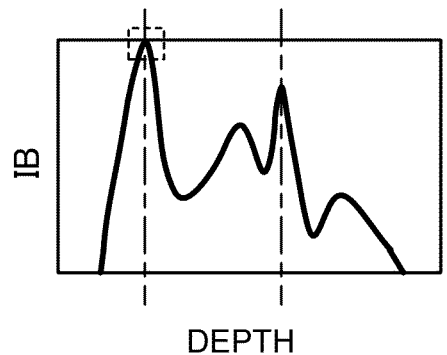

FIGS. 26A and 26B show correction of IB value of adventitia. FIG. 26A is the original histogram, while FIG. 26B is the histogram after correction. It is considered that the IB value of adventitia corresponds to the maximum. A part shown by the rectangle line in 26A as the adventitia is specified. Correction is performed so that the value of the adventitia part is defined as the maximum. Thus, the waveform of IB value is shifted as shown in FIG. 26B. Accordingly, it is possible to provide echo images based on the common measure. As a result, comparison observation can be more accurately made.

Users manually can set a desired position or area on the histogram when the correction can be performed. However, the correction may be automatically performed. It is preferable that a blood vessel lumen part or an adventitia part be specified on the echo image as discussed above. The distribution of IB value is corrected so that the value of a position of the histogram corresponding to the area specified on the echo image defined as the minimum or the maximum. However, as shown in FIG. 25A or 26A, a parts corresponding to blood vessel lumen or adventitia may be specified on the histogram.

Figure 25B:
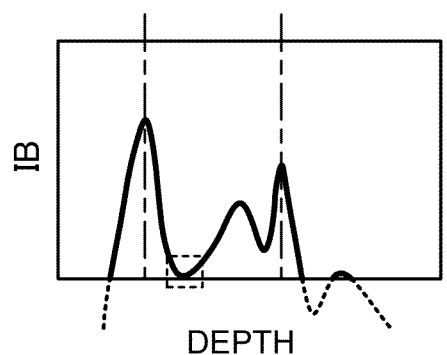

In the embodiment shown FIGS. 25A and 25B, correction is performed so that the waveform of IB value is shifted in parallel. As a result, the IB waveform is maintained. However, the waveform may be deformed in the correction. For example, both the values of the aforementioned blood part and blood vessel part may be corrected. In this case, it is possible to efficiently represent an image with a wide dynamic range. FIGS. 10A and 10B show this correction of IB value. FIGS. 10A and 10B show correction of IB value of blood vessel lumen. FIG. 10A is the histogram of the original IB value, while FIG. 10B is the histogram of IB value after correction. As discussed above, it is considered that the relative minimum of IB value in blood vessel lumen corresponds to blood. For this reason, a part corresponding to the relative minimum is specified by the rectangle line in FIG. 10A. Thus, correction is performed so that the value of this part corresponding to the relative minimum is defined as minimum. As a result, the waveform of IB value can be adjusted as shown in FIG. 10B.

FIGS. 10C and 10D show correction of IB value of adventitia. FIG. 10C is the original histogram, while FIG. 10D is the histogram after correction. It is considered that the IB value of adventitia is the maximum. For this reason, a part corresponding to the adventitia is specified by the rectangle line in FIG. 10C. Thus, correction is performed so that the value of this part corresponding to the adventitia is defined as maximum. As a result, it is possible to efficiently provide a wide dynamic range of IB value as shown in FIG. 10D.

As discussed above, since the echo image of the carotid artery plaque can be displayed not in conventional simple gray scale, which is not easy even for specialists to evaluate plaque properties, but in a colored image, which is easy even for tyros to evaluate plaque properties. For example, it is useful to obtain patients' informed consent. In addition, two images can be arranged side by side and compared with each other, In addition to this, a colored image can be used as one of the two images. Accordingly, time variation can be confirmed. As a result, the symptom improvement and the effect of a medicine can be visually confirmed. Therefore, it is possible to provide an appealing effect to patients. In addition, it is possible to grasp even small time-variation. Accordingly, it is possible to early detect vascular disorder. Therefore, it can be expected to contribute medical care.

Example 1

Validity Confirmation of Statin Group Drug

Examples of the present invention will be described. First, the following description describes an example according to the present invention that confirms of the validity of a statin group drug. In this example, time variation of the properties of a carotid artery plaque is evaluated before and after medication of a statin group drug. Thus, the confirmation of the validity of the medicine according to the present invention is evaluated. Specifically, a statin is given to a patient who has carotid artery plaque. The shape change is observed between at the medication and at the end of medication for one month.

In this specification, the "medicine" is not specifically limited as long as it can improve the properties of carotid artery plaque. That is, the "medicine" is not specifically limited as long as it can be used as hyperlipemia drugs. For example, the "medicine" can be hyperlipemia drugs such as statin drugs, fibrate drugs, EPA preparation, small intestine cholesterol absorption inhibitor, anion exchange resin, and nicotinic acid group medicine.

In this specification, the "statin group drug (statin drugs)" refers to an HMG-CoA reductase inhibitors. For example, examples of the "statin group drug" can be provided by atorvastatin, simvastatin, cerivastatin, pitavastatin, pravastatin, fluvastatin, mevastatin, rosuvastatin, and lovastatin. The statin group drug can be used together with other medicines that have other functions such as ezetimibe (Zetia), which is a cholesterol transporter inhibitor.

Figure 11A:
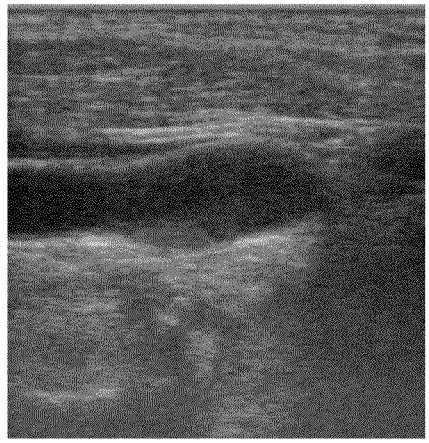
FIGS. 11A and 11B show echo images before and after atorvastatin medication.
Figure 11A:
Figure 11B:
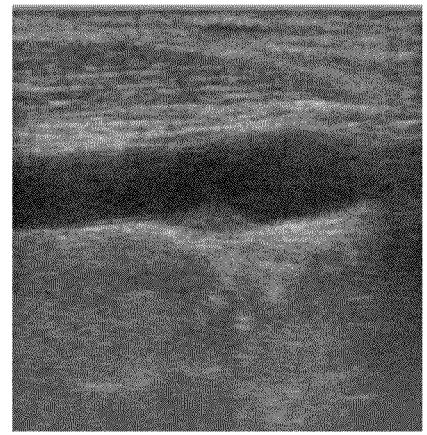

In this specification, the "evaluating method" refers to a method for confirming or evaluating the property change of carotid artery plaque by using the carotid artery echo determining method. For example, in a conventional echo, as shown in FIG. 11, it is not clear whether a statin group drug has an effect on carotid artery plaque. However, in the valuation method according to the present invention, as shown in FIG. 12, it can be visually confirmed that the statin group drug has an effect on the carotid artery plaque. Also, the areas of the colored parts can be compiled. As a result, it is possible to intelligibly show the property change of plaque after medication of the statin group drug as shown in FIG. 13.

(Confirmation of Shape of Carotid Artery Plaque, Evaluation Test)
(Test Patient)

In this example, statin (pitavastatin 2 mg/day) is given for one month to a 55-years-old male patient who has plaque in his carotid artery.
(Determination Method)

Ultrasound backscattering signals of the carotid artery plaque are measured by the IBS method as a carotid artery echo method by using a 12-MHz linear type probe (M12L manufactured by GE) and an echo device (LOGITEC7 manufactured by GE). The relative intensity of the echo signal obtained through the probe is converted by the evaluating program so that the relative intensity is classified in blue, green, yellow, and red in this order from the low intensity to the high intensity.
(Result)

FIGS. 2 to 5 show the carotid artery echo comparison results between before and after the statin is given to the patient for one month. FIGS. 2A and 2C show the echo images before statin medication. FIGS. 2B and 2D show the echo images after statin medication for one month. According to the conventional gray scale display method shown in FIGS. 2A and 2B, the property change of the plaque is unclear. Specifically, according to the gray scale image, in the case where the plaque is indicated by the white closed line, although it can be found that the volume of the plaque is unchanged after one month, other properties cannot be found.

Figure 2A:
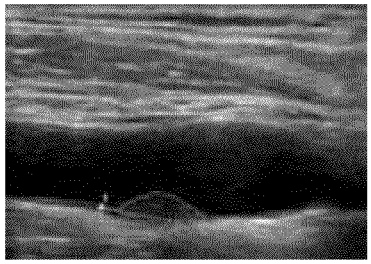
FIG. 2A shows an echo image of carotid artery plaque.
Figure 2B:
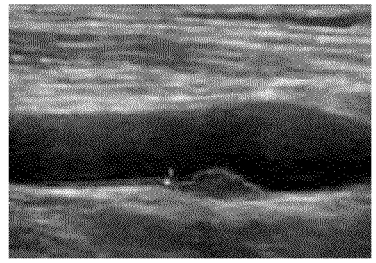
FIG. 2B shows property variation of the plaque one month later after statin medication.
Figure 2C:
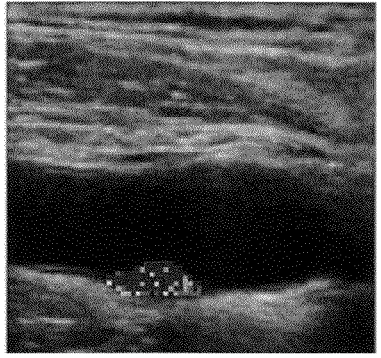
FIG. 2C shows an colored image corresponding to the image shown in FIG. 2A.
Figure 2D:
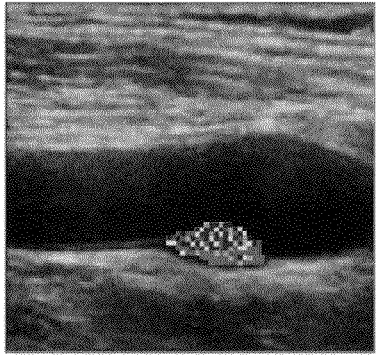
FIG. 2D shows an colored image corresponding to the image shown in 2B.

The images shown in FIGS. 2A and 2B are colored by using the aforementioned evaluating program so that a part of the carotid artery plaque corresponding to the low echo intensity range is displayed in blue, and different colors are assigned to other parts in the aforementioned order with the aforementioned threshold ranges as the intensity is increased. The result is shown in FIGS. 2C and 2D. As shown in FIGS. 2C and 2D, according to the coloring process, the properties of the plaque can be clearly seen. Accordingly, it is possible easily determine the properties of the plaque. FIGS. 3 to 5 show the similar coloring process results of other echo images. FIGS. 2A and 2B show the gray scale display of the echo image obtained by the IBS method. FIGS. 2C and 2D show the result obtained by using the determination method according to the present invention. That is, FIGS. 3A to 5A shows echo images. FIGS. 3B to 5B show colored images that are obtained by the present invention and correspond to the echo images shown in FIGS. 3A to 5A, respectively. FIGS. 3A to 4B are vertical cross-sectional views taken along the carotid artery. FIGS. 5A to 5B are horizontal cross-sectional views of the carotid artery. As shown in FIGS. 3B to 5B, according to the coloring process, the properties of the plaque become very visible. Accordingly, it can be confirmed that the properties can be easily determined. In particular, in the case where the vertical cross-sectional views (FIGS. 3 and 4) and the horizontal cross-sectional view (FIG. 5) of the carotid artery are evaluated, the entire shape and properties (whether unstable or stable) of the plaque in the carotid artery can be more properly determined.

In addition, the tissue image of a specimen that is obtained by carotid endarterectomy (CEA) is compared with the determination method according to the present invention (IB value before the operation). Plaque that is expected as lipid-rich plaque by the determination method according to the present invention is determined as lipid-rich plaque by observation of the obtained specimen. Plaque that is expected as fibrous and stable plaque is determined as plaque that has low lipid and low inflammatory cell infiltration by observation of the obtained specimen.

Accordingly, it can be found that the determination method according to the present invention is better than the conventional echo images in terms of a method for clearly displaying the shape and the properties of plaque. Although the plaque properties can be determined to a certain extent even based on gray scale images, it is said that years of experience is required in the conventional methods. Contrary to this, according to the determination method of the present invention, even tyros can objectively evaluate the properties of plaque with a high degree of reproducibility.

Example 2

Property Evaluation of Carotid Artery Plaque

Figure 7A:
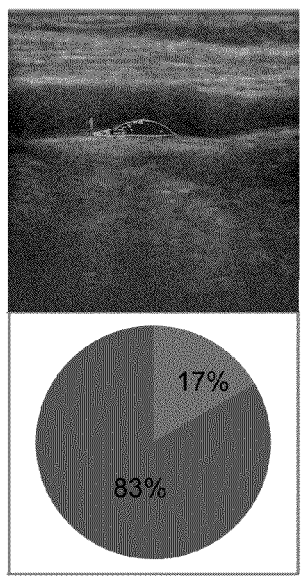
FIG. 7A shows an image including composition of carotid artery plaque shown in 6A.
Figure 7B:
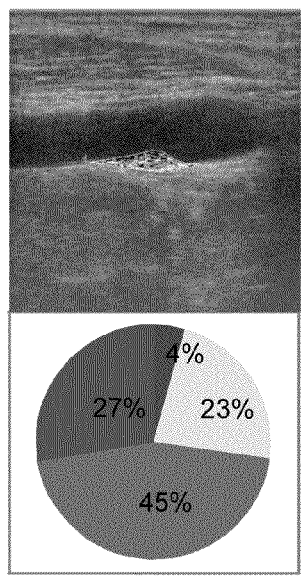
FIG. 7B shows an image including composition of carotid artery plaque shown in 6B.
Figure 7C:
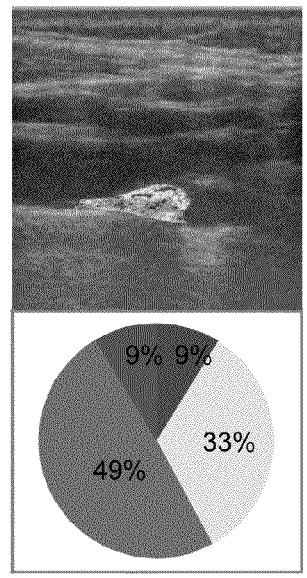
FIG. 7C shows an image including composition of carotid artery plaque shown in 6C.

The following description describes an example that evaluates the properties of carotid artery plaque by using the determination method of the present invention. In this example, three types of carotid artery echoes with different plaque intensity distributions are measured, and are compared with each other by using the method according to the present invention. In this example, carotid artery echo images of patients are obtained. The patients are a patient who has the hypoechoic plaque in the carotid artery (57-years-old female), a patient who has isoechoic plaque (51-years-old male), and a patient who has hyperechoic plaque (73-years-old male). The carotid artery echo images are evaluated by the determination method according to the present invention. FIGS. 6 and 7 show the results. FIGS. 6A to 6C show colored images and specific data of three types of plaque that have intensity distributions corresponding to so-called hypoechoic plaque, isoechoic plaque, and hyperechoic plaque, respectively. FIGS. 7A to 7C show colored images corresponding to the images shown in FIGS. 6A to 6C, respectively, together with circle graphs of the plaque distributions. Although it is difficult to distinguish the hypoechoic plaque and the isoechoic plaque from each other in conventional echo image, according to the determination method of the present invention, it is possible to clearly distinguish the hypoechoic plaque and the isoechoic plaque from each other as shown these figures. In addition, since the areas of the colored parts can be compiled or summed, it is possible to analyze and indicate the properties of plaque as shown in FIG. 7. In this example, the fibrous part is 17%, and the lipid part is 83% in the hypoechoic plaque. In the isoechoic plaque, the calcified part, high fibrous part, fibrous part, and lipid-rich part are 4%, 23%, 45%, and 27%, respectively. In the hyperechoic plaque, the calcified part, high fibrous part, fibrous part, and lipid-rich part are 9%, 33%, 49%, and 9%, respectively. As discussed above, according to this embodiment, it is possible to clearly distinguish the three types of echo images from each other based on the colored images as shown in FIG. 6. In addition, as shown in FIG. 7, it is possible to quantitatively determine the plaque properties.

Example 3

Figure 8A:
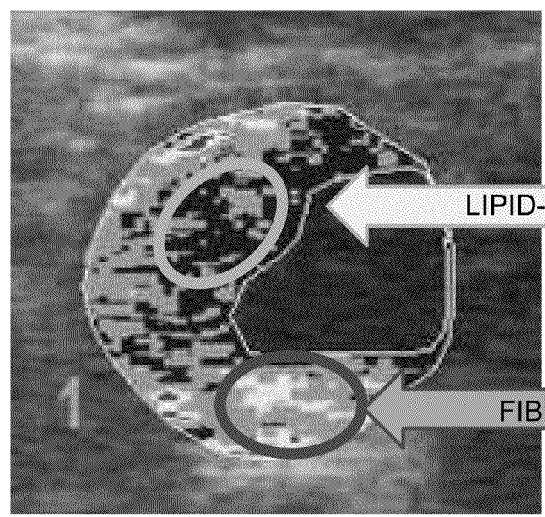
FIG. 8A shows a colored image before CEA.
Figure 8B:
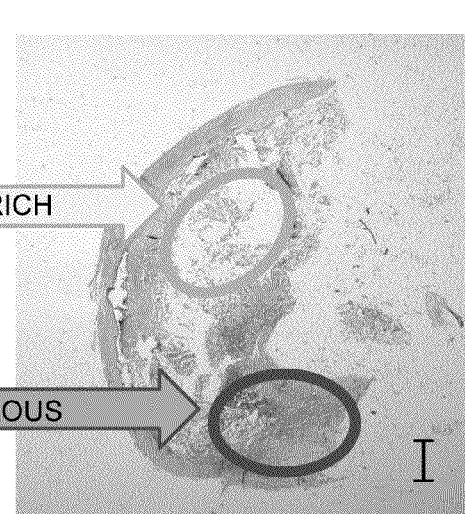
FIG. 8B shows an image corresponding to FIG. 8A with a part to be removed being colored by HE staining.

Comparison between Analysis Result Based on Colored Image, and Actual Tissue Clinical Image To verify whether the analysis result of the plaque properties obtained by the determination method of the present invention agrees with actual histopathological tissue image or not, the plaque property analysis of a CEA patient obtained by the method according to the present invention is compared with actual removed tissue. In this embodiment, the data of CEA patients with high degrees of stenosis in carotid artery (61-years-old male, and 79-years-old male) before the CEA obtained by the carotid artery echo determining method of the present invention is compared with the removed specimen that corresponds to the echo part of carotid artery and is obtained after CEA (HE stained). FIG. 8 show the result of the 61-years-old male. FIG. 9 show the result of the 79-years-old male. FIG. 8A shows a colored image of CEA case. FIG. 8B shows an image corresponding to FIG. 8A with a part to be removed being colored by HE staining. FIG. 9A shows an echo image of CEA case. FIG. 9B shows a colored image corresponding to FIG. 9A. FIG. 9C shows an image corresponding to FIGS. 9A and 9B with a part to be cut being colored by HE staining.

According to these figures, the lipid-rich part plaque part and the fibrous plaque part of the property analysis of the colored image obtained by the present invention have good relationship with the lipid-rich part plaque part and the fibrous plaque part in the image of the actual removed tissue. As a result, the correspondence between the property analysis of the present invention and the actual image is confirmed. Specifically, according to this comparison, the lipid-rich part determined by the determination method of the present invention agrees with the removed specimen of actual blood vessel tissue. Also, in a part that is determined as an advanced stage of fibrosis by the determination method of the present invention, it is found that the part in the removed specimen also results in an advanced stage of fibrosis. As discussed above, the result of analysis evaluation of a carotid artery plaque part obtained by the determination method of the present invention has good relationship with the removed actual tissue specimen of this part. It is found that the determination method of the present invention properly reflects the properties of actual plaque.

In addition, according to evaluation of clinical blood vessel samples, it is supported that the evaluating method of the present invention is closely related not only to carotid artery plaque but also to coronary artery plaque lesion, and has similar relationship with them.

Example 4

Evaluation Test for Determining Effect of Medicine on Arteriosclerosis Patient (1) Patient with Low Degree of Carotid Artery Stenosis First, atorvastatin is given at 10 mg/day for six months to a hyperlipemia patient (51-years-old male) who is a smoker. FIG. 11 show the result of the carotid artery echo before and after medication. FIG. 11A shows the echo image before medication. FIG. 11B shows the echo image after medication. According to these figures, it is difficult to determine whether atorvastatin has effects on the patient or not based on the conventional echo images.

Figure 12A:
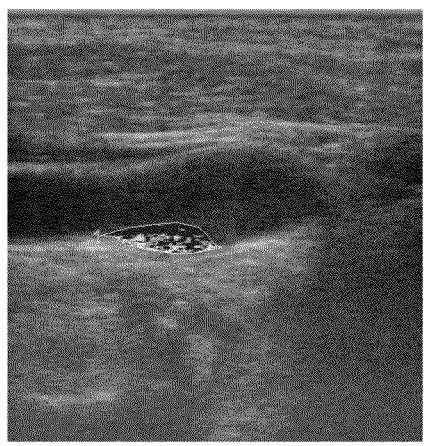
FIG. 12A shows a colored image corresponding to the image shown in FIG. 11A.
Figure 12A:
Figure 12B:
FIG. 12B shows a colored image corresponding to the image shown in FIG. 11B.
Figure 13A:
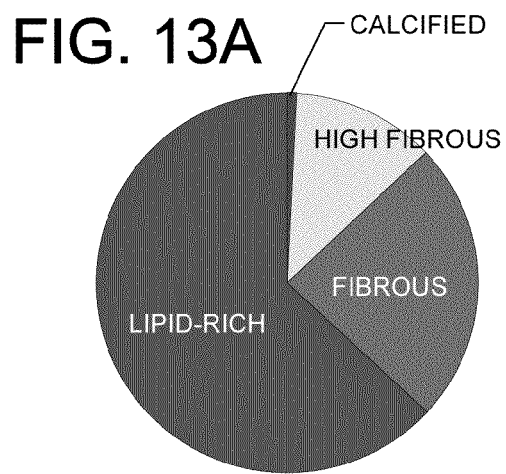
FIGS. 13A and 13B are circle graphs showing the plaque property ratios of the colored images shown in FIGS. 12A and 12B, respectively.
Figure 13B:
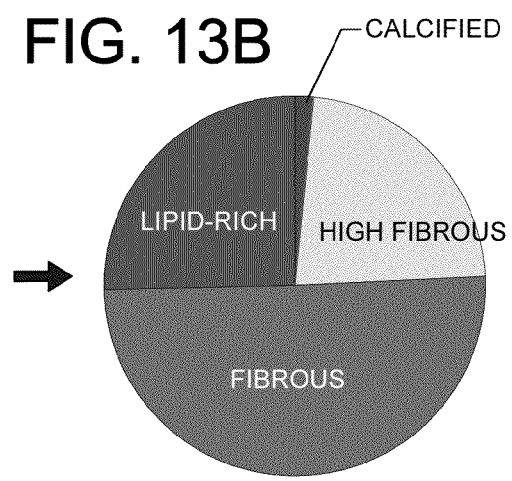

FIG. 12 shows the result of colored carotid artery echo images before and after medication similar to FIG. 11 that is colored by the determination method of the present invention. FIG. 12A shows the colored image corresponding to the image shown in FIG. 11A. FIG. 12B shows the colored image corresponding to the image shown in FIG. 11B. According to these figures, it is clearly found that atorvastatin has effects on the patient. In addition, in the case where the areas of the colored parts can be compiled or summed, it is possible to analyze the properties of plaque. FIGS. 13A and 13B are circle graphs showing the plaque classification ratios in the colored images shown in FIGS. 12A and 12B, respectively. In each of these figures, the areas of the colored parts in each of the colored images shown in FIG. 12 are summed. Thus, it is possible to show the comparison between the properties (composition) of plaque before and after medication, in other words, how the composition of plaque changes. According to these figures, it is clearly confirmed that the lipid in the plaque decreases by half after medication of atorvastatin for six months. As discussed above, it is confirmed by using the determination method of the present invention that the effect of a medicine on a patient can be properly determined.

(2) Patient with High Degree of Carotid Artery Stenosis

Secondly, pitavastatin is given at 2 mg/day for three months to a patient (55-years-old male) who has high degree, approximately 50% of carotid artery stenosis. The LDL-C value, HDL-C value, and TG value before medication are 138, 64, and 94, respectively. After medication, the LDL-C value, HDL-C value, and TG value become 106, 68, and 67 respectively. In order to further lower the LDL-C value and observe the carotid artery echo variation, pitavastatin and ezetimibe are given for three months to the patient at 2 mg/day and 10 mg/day, respectively. As a result, the LDL-C value and HDL-C value become 75 and 76, respectively. Thus, the LDL-C value greatly decreases.

Figure 14A:
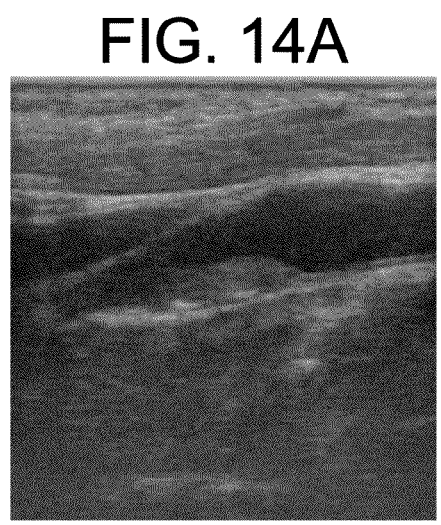
FIG. 14A shows an echo image before pitavastatin medication.
Figure 14B:
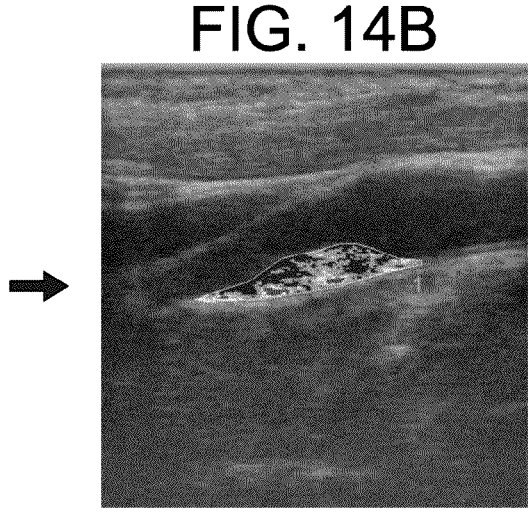
FIG. 14B shows a colored image corresponding to the image shown in FIG. 14A.
Figure 15A:
FIG. 15A shows an echo image after pitavastatin medication.
Figure 15B:
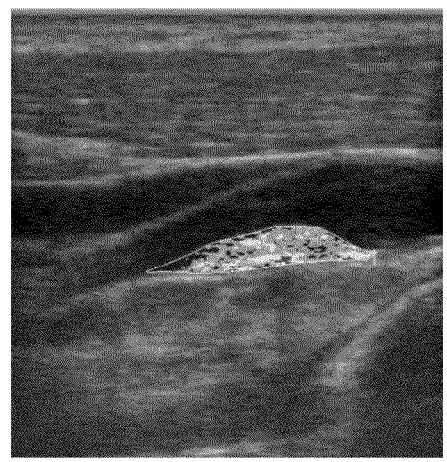
FIG. 15B shows a colored image corresponding to the image shown in FIG. 15A.

FIGS. 14A and 14B are echo images before medication of pitavastatin. FIGS. 15A and 15B are echo images after the medication for six-months. FIGS. 14A and 15A show conventional echo images. FIGS. 14B and 15B show colored images corresponding to the images of FIGS. 14A and 15A, respectively. According to comparison between conventional carotid artery echo images before and after medication, variation cannot be clearly seen between echo images (FIGS. 14A and 15A) before and after the medication of pitavastatin for six months.

Figure 16A:
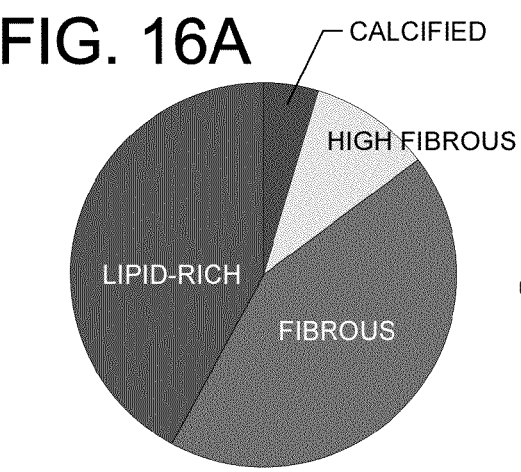
FIGS. 16A and 16B are circle graphs showing the plaque property ratios in the case of FIGS. 14B and 15B, respectively.
Figure 16B:
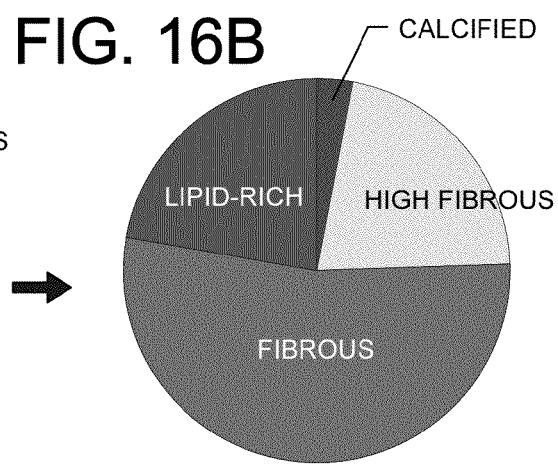

Contrary to this, according to the carotid artery echo determining method of the present invention, although variation cannot be seen in plaque size, the difference can be clearly seen between the properties of the plaque before and after the medication. That is, the carotid artery echo image (FIG. 14B) before the medication varies to the carotid artery echo image shown in FIG. 15B after the medication. For comparison of the compiled or summed areas of colored parts in the echo images before and after the medication, FIGS. 16A and 16B show the ratios of the plaque properties in FIGS. 14B and 15B, respectively. According to these figures, it is confirmed that the medication increase the fibrous plaque part so that the ratio of lipid decreases by half. As discussed above, the property variation of plaque can be clearly checked by the carotid artery echo determining method of the present invention. Accordingly, it is clear that the carotid artery echo determining method of the present invention can be used as a method for determining/evaluating effects of a statin group drug.

According to the carotid artery plaque property determining method of the present invention, it is possible to properly determine the properties of carotid artery plaque, in other words, whether the carotid artery plaque is stable plaque or unstable plaque, and to properly confirm the property variation of carotid artery plaque. Accordingly, if it is determined that a patient has unstable plaque, a statin group drug can be given to the patient so that the LDL-C value in blood can be lowered. As a result, it becomes possible to stabilize the properties of the plaque at an early stage. Therefore, since the patient can be treated early, it is expected to greatly reduce the incidence rate of myocardial infarct or cerebral infarction.

The method according to the present invention can be used for carotid artery echo, which is widely used in many hospitals. Accordingly, the method according to the present invention is very convenient. Therefore, the method according to the present invention is useful as a diagnosis method for carrying out tests on many patients. In addition, according to the method of the present invention, it is possible to evaluate effects of statin drugs on a patient. As a result, it will become possible to select a suitable statin group drug for the patient. In addition, it is possible to properly evaluate the stage or improvement of arteriosclerosis. Therefore, it is possible to provide a very useful carotid artery echo diagnosis method that can be easily clinically used.

INDUSTRIAL APPLICABILITY

Since a carotid-artery-plaque ultrasound-imaging method, a carotid-artery-plaque evaluating device, a carotid-artery-plaque evaluating program, and a computer-readable storage medium according to the present invention can classify the composition of carotid artery plaque and display the classified compositions in colors in a carotid artery echo image, they can be suitably used to evaluate the properties of plaque based on the carotid artery echo image. Accordingly, the colored image can be used to obtain patients' informed consent. In addition, the present invention is suitable for grasp of symptom history or the progression of improvement, validity evaluation of hyperlipemia drugs, and the like. Although the title of invention includes carotid artery plaque, the present can be applied to tissues other than carotid artery plaque.

REFERENCE SIGNS LIST 100, 200 . . . Carotid artery plaque valuating device
10, 10B . . . Obtaining portion
12 . . . Image memory
20 . . . Calculation portion
22 . . . Coloring portion
30 . . . Display portion
40 . . . Memory portion
50 . . . Operation portion
60 . . . User interface display of carotid artery plaque evaluating program
61 . . . Operation area
62 . . . Image display area
63 . . . "File selection" tab
64 . . . "Analysis display" tab
65 . . . Switching radio button
66 . . . "Two-area display mode" check box
70 . . . Setting display
71 . . . "Analysis result" tab
72 . . . "Setting" tab
73 . . . Color assigning portion
74 . . . Color selecting button
75 . . . Adjustment box
76 . . . Correction radio button
80 . . . Ultrasonic probe
81 . . . Raw signal output portion
82 . . . Controller
UD . . . Echo device
PC . . . Computer
RI . . . Specified area
CR . . . Color assignment area

The invention claimed is:

1. A carotid-artery-plaque ultrasound-imaging method for producing an echo image of carotid artery plaque comprising:

obtaining raw signals of echo signals corresponding to pixels that compose an echo image of carotid artery plaque, the echo signals being obtained when the echo image is obtained by a carotid artery echo integrated backscatter method, wherein said raw signals are integrated amounts per unit time of said echo signals;

referencing the relationship between coloring ranges and colors, the available full range of the integrated amount being previously divided into the coloring ranges, and the colors being assigned to the coloring ranges, classifying the pixels, which are included in said obtained echo image, into the coloring ranges in accordance with the integrated amounts corresponding to the pixels, and coloring each of the pixels of the echo image in one of the colors corresponding to the range of the each of the pixels;

displaying said colored echo image on a display;

specifying an area on said colored echo image;

correcting the raw signals of the echo image with a relative maximum value or a relative minimum value of a distribution of the raw signals in said specified area;

coloring said echo image based on the corrected raw signals to obtain a corrected colored echo image, by referencing the relationship between coloring ranges and colors; and displaying the corrected colored echo image on the display.

2. The carotid-artery-plaque ultrasound-imaging method according to claim 1, wherein said coloring ranges for classifying the integrated amount are
a) the range of 0 to −55 dB,
b) the range of −55 to −65 dB,
c) the range of −65 to −75 dB, and
d) the range of −75 dB or less.

3. The carotid-artery-plaque ultrasound-imaging method according to claim 2, wherein the colors corresponding, to the coloring ranges are
a) red assigned to the range of 0 to −55 dB,
b) yellow assigned to the range of −55 to −65 dB,
c) green assigned to the range of −65 to −75 dB, and
d) blue assigned to the range of −75 dB or less.

4. The carotid-artery-plaque ultrasound-imaging method according to claim 1, wherein said echo image includes information on arteriosclerosis.

5. The carotid-artery-plaque ultrasound-imaging method according to claim 1, wherein said echo image includes information on effect of a medicine on carotid artery plaque.

6. The ultrasound-imaging method according to claim 5, wherein said medicine is a statin group drug.

7. The ultrasound-imaging method according to claim 6, wherein said statin group drug is selected from the group consisting of atorvastatin, simvastatin, cerivastatin, pitavastatin, pravastatin, fluvastatin, mevastatin, rosuvastatin, and lovastatin.

8. A carotid-artery-plaque evaluating device comprising:
a computer programmed to:
obtain raw signals of echo signals corresponding to reference areas that compose an echo image of carotid artery plaque, the echo signals being obtained when the echo image is obtained by a carotid artery echo integrated backscatter method, wherein said raw signals are integrated amounts per unit time of said echo signals;
store in a memory the relationship between coloring ranges and colors, the available full range of the raw signals being previously divided into the coloring ranges, and the colors being assigned to the coloring ranges;
classify the reference areas, which are included in said echo image, into the coloring ranges in accordance with the raw signals corresponding to the reference areas by referencing said memory, and coloring each of the reference areas of the echo image in one of the colors corresponding to the raw signal of each of the reference areas;
display the echo image that has been colored on a display;
set any point or an area on the colored echo image;
correct the raw signals of the echo image with a relative maximum value or a relative minimum value of a distribution of the raw signals in the point or area that is set;
color the echo image based on the corrected raw signals to obtain a corrected colored echo image, by referencing the relationship between coloring ranges and colors; and
display the corrected colored echo image on the display.

9. The carotid-artery-plaque evaluating, device according to claim 8, wherein said reference areas, which compose the echo image, are pixels that compose the echo image.

10. The carotid-artery-plaque evaluating device according to claim 8, wherein said computer is programmed to correct the raw signal so that the value corresponding to a blood part in said echo image is set to the minimum of the available full range of the raw signal.

11. The carotid-artery-plaque evaluating device according to claim 8, wherein said display is configured to display the integrated amounts in histogram form.

12. The carotid-artery-plaque evaluating device according to claim 11,
wherein, in the case where the echo image is displayed on said display, when a blood vessel lumen is set, said computer is programmed to correct the integrated amount corresponding to the position of the blood vessel lumen to the minimum of the integrated amount.

13. The carotid-artery-plaque evaluating device according to claim 11,
wherein, in the case where the echo image is displayed on said display, when adventitia is set, said computer is programmed to correct the integrated amount corresponding to the position of the adventitia to the maximum of the integrated amount.

14. The carotid-artery-plaque evaluating device according to claim 8,
wherein the computer is programmed to set an area of carotid artery plaque on the echo image that is displayed on said display, and
wherein the computer is programmed to color the carotid artery plaque based on the set area when the carotid artery plaque is displayed.

15. The carotid-artery-plaque evaluating device according to claim 8, wherein the computer is programmed to display the occupancy ratio between colored areas that are colored in graph form on said display.

16. The carotid-artery-plaque evaluating, device according to claim 8,
wherein said display is configured to display divided, display areas that display two echo images on the screen of said display, and
wherein one of divided display areas is configured to display an uncolored echo image, and another divided display area is configured to display the colored echo image that corresponds to the uncolored echo image and is colored.

17. A non-transitory computer readable medium storing a carotid-artery-plaque evaluating program for causing a computer to execute:
an obtaining function that obtains raw signals of echo signals corresponding to areas that compose an echo image of carotid artery plaque, the echo signals being obtained when the echo image is obtained by a carotid artery echo integrated backscatter method, wherein said raw signals are integrated amounts per unit time of said echo signals;
a table-storing function that stores the relationship between coloring ranges and colors, the available full range of the raw signal being previously divided into the coloring ranges, and the colors being assigned to the coloring ranges;

a coloring function that classifies the areas, which are included in said echo image, into the coloring ranges in accordance with the raw signals corresponding to the areas by referencing said table-storing function, and colors each of the areas of the echo image in one of the colors corresponding to the raw signal of the each of the areas;

a display function that displays said echo image colored by said coloring function;

an operation function that specifies an area on the colored echo image;

a correction function that corrects the raw signals of the echo image with a relative maximum value or a relative minimum value of a distribution of the raw signals in an area that is specified with said operation function;

a second coloring function that colors the echo image based on the corrected raw signals to obtain a corrected colored echo image, by referencing the relationship between coloring ranges and colors; and a second display function that displays the corrected colored echo image on the display.

* * * * *